US010995348B2

United States Patent
Terai et al.

(10) Patent No.: US 10,995,348 B2
(45) Date of Patent: *May 4, 2021

(54) METHOD OF PRODUCING LIPID

(71) Applicant: Kao Corporation, Tokyo (JP)

(72) Inventors: Mika Terai, Sakai (JP); Akihito Kawahara, Wakayama (JP); Tatsuro Ozaki, Wakayama (JP)

(73) Assignee: Kao Corporation, Tokyo (JP)

( * ) Notice: Subject to any disclaimer, the term of this patent is extended or adjusted under 35 U.S.C. 154(b) by 154 days.

This patent is subject to a terminal disclaimer.

(21) Appl. No.: 16/094,080

(22) PCT Filed: Apr. 4, 2017

(86) PCT No.: PCT/JP2017/014139
§ 371 (c)(1),
(2) Date: Oct. 16, 2018

(87) PCT Pub. No.: WO2017/195505
PCT Pub. Date: Nov. 16, 2017

(65) Prior Publication Data
US 2019/0376099 A1 Dec. 12, 2019

(30) Foreign Application Priority Data
May 10, 2016 (JP) .............................. JP2016-094479

(51) Int. Cl.
C12P 7/64 (2006.01)
C12N 9/10 (2006.01)
C12N 1/20 (2006.01)

(52) U.S. Cl.
CPC .................. C12P 7/64 (2013.01); C12N 1/20 (2013.01); C12N 9/1029 (2013.01); C12Y 203/01041 (2013.01)

(58) Field of Classification Search
None
See application file for complete search history.

(56) References Cited

U.S. PATENT DOCUMENTS

| 10,066,248 | B2 | 9/2018 | Sugihara et al. | |
|---|---|---|---|---|
| 2002/0066123 | A1 | 5/2002 | Jaworski et al. | |
| 2009/0298143 | A1 | 12/2009 | Roessler et al. | |
| 2013/0102040 | A1 | 4/2013 | Radakovits et al. | |
| 2013/0280793 | A1 | 10/2013 | Brown et al. | |
| 2013/0344549 | A1* | 12/2013 | Roberts | C12P 7/64 435/134 |
| 2016/0046902 | A1* | 2/2016 | Roberts | C12P 7/6409 435/471 |
| 2017/0044580 | A1 | 2/2017 | Sugihara et al. | |
| 2018/0135084 | A1 | 5/2018 | Kawahara et al. | |
| 2019/0338318 | A1 | 11/2019 | Terai et al. | |
| 2019/0376099 | A1* | 12/2019 | Terai | C12Y 203/01041 |

FOREIGN PATENT DOCUMENTS

| JP | 2002-503961 A | 2/2002 |
|---|---|---|
| JP | 2011-505838 A | 3/2011 |
| JP | 2015-517811 A | 6/2015 |
| WO | WO 98/54954 A1 | 12/1998 |
| WO | WO 2009/076559 A1 | 6/2009 |
| WO | WO 2013/162648 A1 | 10/2013 |
| WO | WO 2015/133305 A1 | 9/2015 |
| WO | WO 2015/200335 A1 | 12/2015 |
| WO | WO 2016/190238 A1 | 1/2016 |
| WO | WO 2017/022740 A1 | 2/2017 |

OTHER PUBLICATIONS

GenEmbl Accession No. JU980979, published May 16, 2012 (Year: 2012).*
International Search Report (ISR) for PCT/JP2017/014139; I.A. fd Apr. 4, 2017, dated Jul. 4, 2017 from the Japan Patent Office, Tokyo, Japan.
International Preliminary Report on Patentability (IPRP), Chapter I of the Patent Cooperation Treaty, including the Written Opinion for PCT/JP2017/014139; I.A. fd Apr. 4, 2017, dated Nov. 13, 2018, by the International Bureau of WIPO, Geneva, Switzerland.
Liu, X et al., "Fatty acid production in genetically modified cyanobacteria," Proc Natl Acad Sci U S A. Apr. 26, 2011;108(17):6899-904. doi: 10.1073/pnas.1103014108. Epub Apr. 11, 2011, National Academy of Sciences, Washington, DC.
Borges, L et al., "Effects of flocculants on lipid extraction and fatty acid composition of the microalgae *Nannochloropsis oculata* and *Thalassiosira weissflogii*," Biomass and Bioenergy 35(10): 4449-4454, Oct. 15, 2011, available online Sep. 22, 2011, Elsevier.
Excerpted file history, U.S. Appl. No. 16/475,178: Notice of Allowance (dated Aug. 3, 2020); Reply to restriction requirement (dated Jul. 2, 2020); Restriction requirement (dated May 13, 2020); and Preliminary amendment (dated Jul. 1, 2019).

* cited by examiner

*Primary Examiner* — Richard C Ekstrom
(74) *Attorney, Agent, or Firm* — Sterne, Kessler, Goldstein & Fox P.L.L.C.

(57) ABSTRACT

A method of producing lipids, comprising the steps of:
culturing a transformant in which the expression of a gene encoding at least any one of the following proteins (A) to (D) is enhanced in a cyanobacteria cell, and
producing fatty acids or lipids containing these fatty acids as components.
(A) a protein consisting of the amino acid sequence set forth in SEQ ID NO: 1;
(B) a protein consisting of an amino acid sequence having 60% or more identity with the amino acid sequence of the protein (A), and having β-ketoacyl-ACP synthase activity;
(C) a protein consisting of the amino acid sequence set forth in SEQ ID NO: 44; and
(D) a protein consisting of an amino acid sequence having 60% or more identity with the amino acid sequence of the protein (C), and having β-ketoacyl-ACP synthase activity.

20 Claims, No Drawings
Specification includes a Sequence Listing.

SEQUENCE LISTING

```
<160> NUMBER OF SEQ ID NOS: 45

<210> SEQ ID NO 1
<211> LENGTH: 475
<212> TYPE: PRT
<213> ORGANISM: Nannochloropsis oculata

<400> SEQUENCE: 1

Met Met Glu Lys Leu Thr Leu Ala Val Val Gly Ser Leu Ala Leu Thr
1               5                   10                  15

Ser Ala Phe Gln Pro Ser Ser Phe Phe Leu Arg Gln Thr Ser Ser Val
            20                  25                  30

Ser Ser Ser Ser Ser Ser Ser Arg Thr Val Arg Arg Ala Ser Gly Glu
        35                  40                  45

Val Ser Met Ala Asp Leu Pro Pro Leu Val Arg Lys Arg Val Val Ile
    50                  55                  60

Thr Gly Val Gly Ala Val Ser Pro Leu Gly Trp Gly Asp Asp Phe Trp
65                  70                  75                  80

Asn Gly Leu Val Glu Gly Arg Ser Gly Ile Val Arg Leu Pro Ser Trp
                85                  90                  95

Ala Asp Glu Tyr Pro Ala Arg Ile Gly Gly Leu Val Pro Asp His Phe
            100                 105                 110

Lys Pro Ser Asp Tyr Met Asn Ala Lys Glu Val Lys Arg Gln Ala Arg
        115                 120                 125

Phe Thr His Phe Ala Met Ala Ala Arg Met Ala Val Glu Asp Ala
    130                 135                 140

Lys Leu Asp Leu Glu Lys Val Asp Arg Ser Arg Ala Gly Cys Met Ile
145                 150                 155                 160

Gly Ser Gly Ile Gly Gly Val Glu Ile Phe Glu Lys Asn Cys Gly Glu
```

```
              165                 170                 175
Phe Asp Lys Lys Gly Gly Leu Pro Gly Leu Lys Ala Val Ser Pro
            180                 185                 190
Phe Leu Ile Pro Ala Leu Ile Ala Asn Thr Ala Ala Gly Thr Val Ala
            195                 200                 205
Ile Glu Leu Gly Leu Lys Gly Pro Asn Tyr Cys Ser Val Ser Ala Cys
            210                 215                 220
Ala Ser Gly Thr His Thr Ile Gly Asp Ala Phe Phe Leu Gln Asn
225                 230                 235                 240
Gly Met Ala Asp Val Cys Val Thr Gly Thr Glu Ala Ala Ile Thr
                245                 250                 255
Pro Leu Cys Phe Ala Gly Phe Val Ala Ile Arg Ala Leu Thr Thr Ser
                260                 265                 270
Gly Asn Asp Asp Pro Thr Lys Ala Ser Lys Pro Phe Asp Lys Asn Arg
                275                 280                 285
Ala Gly Phe Val Met Ala Glu Gly Ala Gly Met Leu Val Leu Glu Thr
            290                 295                 300
Glu Glu His Ala Lys Ala Arg Gly Ala Thr Ile Tyr Ala Glu Leu Ala
305                 310                 315                 320
Gly Tyr Gly Ala Ser Cys Asp Ala His His Ile Thr Ala Pro His Pro
                325                 330                 335
Glu Gly Glu Gly Leu Ala Asn Ala Met Asn Met Ala Leu Thr Ser Ala
            340                 345                 350
Gly Leu Lys Pro Thr Asp Val Asp Tyr Ile Asn Ala His Gly Thr Ser
            355                 360                 365
Thr Ala Tyr Asn Asp Lys Phe Glu Thr Leu Ala Ile His Arg Val Phe
    370                 375                 380
Gly Glu His Ala Lys Lys Leu Lys Val Ser Ser Ile Lys Ser Met Thr
385                 390                 395                 400
Gly His Ser Leu Gly Ala Ala Gly Ala Phe Glu Ala Val Ala Cys Ala
                405                 410                 415
Lys Ala Ile Lys Glu Gly Ile Ile Pro Pro Thr Ile Asn Tyr Glu Thr
            420                 425                 430
Pro Asp Pro Asp Cys Asp Leu Asp Tyr Val Pro Asn Lys Ala Ile Lys
            435                 440                 445
His Asp Val Asn Val Ala Ile Ser Asp Asn Leu Gly Phe Gly Gly His
        450                 455                 460
Asn Ala Ala Leu Val Phe Lys Lys Tyr Val Ala
465                 470                 475

<210> SEQ ID NO 2
<211> LENGTH: 1428
<212> TYPE: DNA
<213> ORGANISM: Nannochloropsis oculata

<400> SEQUENCE: 2
atgatggaga agctgaccct cgcagtggtg ggctcccttg ccctgacttc ggccttccag      60
ccctcgtcct tcttcctccg gcagacttcc tccgtcagca gcagcagcag cagcagcagg     120
actgtgcgtc gtgcatcagg ggaagtgagc atggcggact tgcccccgct tgtccgcaag     180
agggtggtga tcacgggtgt cggcgccgtg tctcctctcg ggtggggaga cgacttctgg     240
aacggtctcg tggagggaag gagcggcatt gtccgcctcc cttcgtgggc ggacgagtac     300
cccgcgcgaa tcggaggctt ggtcccggat cactttaagc cgagcgacta catgaatgcc     360
```

| aaggaggtga aacgacaggc ccgcttcacc cattttgcca tggcagctgc ccgtatggcc | 420 |
| gtggaagacg ccaagctcga cctggagaag gtggaccgct cgcgtgccgg gtgcatgata | 480 |
| ggatccggca ttggtggtgt agaaatcttc gagaaaaact gtggggaatt cgacaagaag | 540 |
| ggcggagggc tccctggcct caaggctgtc tcccccttcc tgattccggc cctcatcgcc | 600 |
| aacaccgcag ccgggacagt ggctattgaa ctcggcttga agggcccgaa ctactgctct | 660 |
| gtctccgcct gcgcctcggg cacgcatacc atcggtgatg ccttcttctt cctccaaaac | 720 |
| ggcatggcgg acgtttgtgt aacgggcggg acggaagccg ccatcacccc cctctgtttt | 780 |
| gcgggatttg tcgccattcg cgcccttacc accagtggca acgacgaccc caccaaggcc | 840 |
| tccaagccgt cgacaagaa ccgagccggt ttcgttatgg ccgagggagc ggggatgctc | 900 |
| gtccttgaga cggaggaaca cgcgaaggcc cgaggtgcca ccatctatgc cgagcttgct | 960 |
| ggctacggcg catcctgcga cgcccaccac atcaccgccc ccatcccga aggcgagggg | 1020 |
| ctggcgaacg cgatgaatat ggctctgacg tccgccggcc tcaagcctac ggacgtggac | 1080 |
| tacattaatg cccatggaac cagcacggcc tacaacgaca aattcgagac gctggccatt | 1140 |
| caccgcgtct ttggcgagca cgccaagaag ctgaaggttt cttccatcaa gtcaatgact | 1200 |
| ggtcactccc tcggggccgc cggtgccttc gaggccgtgg cgtgcgcgaa ggcaatcaag | 1260 |
| gagggcatca tcccgcccac catcaactac gagactcccg atccagactg cgacttggac | 1320 |
| tatgttccca acaaggcgat caagcacgac gtgaatgtgg ccatctccga taacctgggc | 1380 |
| ttcggcgggc acaacgcggc tttggtcttc aagaagtatg ttgcctag | 1428 |

```
<210> SEQ ID NO 3
<211> LENGTH: 33
<212> TYPE: DNA
<213> ORGANISM: Artificial Sequence
<220> FEATURE:
<223> OTHER INFORMATION: primer pUC118/slr0168up-F

<400> SEQUENCE: 3
```

| ggatcctcta gagtcatcgc ctgttggcct acc | 33 |

```
<210> SEQ ID NO 4
<211> LENGTH: 35
<212> TYPE: DNA
<213> ORGANISM: Artificial Sequence
<220> FEATURE:
<223> OTHER INFORMATION: primer Kmr/slr0168up-R

<400> SEQUENCE: 4
```

| ttcgctgggt ttatctaccg ttcaaattct gtggg | 35 |

```
<210> SEQ ID NO 5
<211> LENGTH: 841
<212> TYPE: DNA
<213> ORGANISM: Synechocystis sp. PCC6803

<400> SEQUENCE: 5
```

| atcgcctgtt ggcctaccct ccgccgatc gcctaaatct cagcgccaag agtagttccc | 60 |
| tcaacaccag tattctgctc agcagtgacc tattcaatca ggaaggggga attgtaacag | 120 |
| ccaactatgg ctttgatggt tatatgggaa ttcccggtat ggatggcacc gatgcggaat | 180 |
| cccaacagat tgcctttgac aacaatgtgg cctggaataa cctgggggat tgtccacca | 240 |
| ccacccaacg ggcctacact tcggctatta gcacagacac agtgcagagt gtttatggcg | 300 |
| ttaatctgga aaaaaacgat aacattccca ttgttttttgc gtggcccatt tttcccacca | 360 |

```
cccttaatcc cacagatttt caggtaatgc ttaacacggg ggaaattgtc accccggtga    420
tcgcctcttt gattcccaac agtgaataca acgaacggca aacggtagta attacgggca    480
attttggtaa tcgtttaacc ccaggcacgg agggagcgat ttatcccgtt ccgtaggca     540 cagtgttgga cagtactcct ttggaaatgg tgggacccaa cggcccggtc agtgcggtgg    600
gtattaccat tgatagtctc aaccccctacg tggccggcaa tggtcccaaa attgtcgccg   660
ctaagttaga ccgcttcagt gacctggggg aaggggctcc cctctggtta gccaccaatc    720
aaaataacag tggcggggat ttatatggag accaagccca atttcgtttg cgaatttaca    780
ccagcgccgg ttttttcccc gatggcattg ccagtttact acccacagaa tttgaacggt    840
a                                                                    841
```

```
<210> SEQ ID NO 6
<211> LENGTH: 35
<212> TYPE: DNA
<213> ORGANISM: Artificial Sequence
<220> FEATURE:
<223> OTHER INFORMATION: primer Kmr/slr0168down-F

<400> SEQUENCE: 6
ggaatttgta tcgatagcgg aagatattac gggac                                35

<210> SEQ ID NO 7
<211> LENGTH: 34
<212> TYPE: DNA
<213> ORGANISM: Artificial Sequence
<220> FEATURE:
<223> OTHER INFORMATION: primer pUC118/slr0168down-R

<400> SEQUENCE: 7
gcatgcctgc aggtcaatca cgttgggtcc caag                                 34

<210> SEQ ID NO 8
<211> LENGTH: 979
<212> TYPE: DNA
<213> ORGANISM: Synechocystis sp. PCC6803

<400> SEQUENCE: 8
agcggaagat attacgggac ggacagttat cctaacccaa actggtgttg attatgaaat     60
tcccggcttt ggtctggtgc aggtgttggg gctggcggat ttggccgggg ttcaggacag    120
ctatgacctg acttacatcg aagatcatga caactattac gacattatcc tcaaagggga   180
cgaagccgca gttcgccaaa ttaagagggt tgctttgccc tccgaagggg attattcggc    240
ggtttataat cccggtggcc ccggcaatga tccagagaat ggtcccccag ggcccttttac   300 tgtgtccagt agtccccagg taattaaggt aacggatacc atcggccagc ccaccaaagt    360
ctcctatgtg gaagtggatg gccccgtatt gcgtaatccc ttcagtggta ctcccattgg    420
gcaagaggtg ggtttagcgg ttaaagatct ggccacaggt catgaaattt atcagtacac    480
tgacccagat gggaaggtat tttatgcttc ctttgctgcc gctgatgacc aagccacgga    540
tttaaccacg gcgatcgcca atcccacggc catcgattta attaacgcca ggggatttac    600
ggcgggtagt tccgtcaccg tatcgggttc ctacagtcgg gaagcctttt ttgatggatc    660
catgggtttt tatcgacttc tggacgataa cggtgcagtg ctagatccct taacaggtgg   720
tgtaatcaac ccaggacagg taggttatca agaagcagct ttggcagata gcaatcgttt    780
gcaagccact ggctccaccc taacggcaga agacctagaa accagagcat tttccttcaa    840
```

| | |
|---|---|
| tattttgggt ggcgagttgt atgcgccatt tttaacggtt aatgacagtc tttccggtat | 900 |
| taatcagact tattttgcct ttgggtcggc caacccagat ggcatcagcc acagcacaaa | 960 |
| cttgggaccc aacgtgatt | 979 |

<210> SEQ ID NO 9
<211> LENGTH: 18
<212> TYPE: DNA
<213> ORGANISM: Artificial Sequence
<220> FEATURE:
<223> OTHER INFORMATION: primer Kmr-F

<400> SEQUENCE: 9

| | |
|---|---|
| gataaaccca gcgaacca | 18 |

<210> SEQ ID NO 10
<211> LENGTH: 18
<212> TYPE: DNA
<213> ORGANISM: Artificial Sequence
<220> FEATURE:
<223> OTHER INFORMATION: primer Kmr-R

<400> SEQUENCE: 10

| | |
|---|---|
| atcgatacaa attcctcg | 18 |

<210> SEQ ID NO 11
<211> LENGTH: 1489
<212> TYPE: DNA
<213> ORGANISM: Artificial Sequence
<220> FEATURE:
<223> OTHER INFORMATION: kanamycin resistance gene

<400> SEQUENCE: 11

| | |
|---|---|
| gataaaccca gcgaaccatt tgaggtgata ggtaagatta taccgaggta tgaaaacgag | 60 |
| aattggacct ttacagaatt actctatgaa gcgccatatt taaaaagcta ccaagacgaa | 120 |
| gaggatgaag aggatgagga ggcagattgc cttgaatata ttgacaatac tgataagata | 180 |
| atatatcttt tatatagaag atatcgccgt atgtaaggat ttcaggggc aaggcatagg | 240 |
| cagcgcgctt atcaatatat ctatagaatg gcaaagcat aaaaacttgc atggactaat | 300 |
| gcttgaaacc caggacaata accttatagc ttgtaaattc tatcataatt gtggtttcaa | 360 |
| aatcggctcc gtcgatacta tgttatacgc caactttcaa aacaactttg aaaaagctgt | 420 |
| tttctggtat ttaaggtttt agaatgcaag gaacagtgaa ttggagttcg tcttgttata | 480 |
| attagcttct tggggtatct ttaaatactg tagaaaagag gaaggaaata taaatggct | 540 |
| aaaatgagaa tatcaccgga attgaaaaaa ctgatcgaaa ataccgctg cgtaaaagat | 600 |
| acggaaggaa tgtctcctgc taaggtatat aagctggtgg gagaaaatga aaacctatat | 660 |
| ttaaaaatga cggacagccg gtataaaggg accacctatg atgtggaacg ggaaaaggac | 720 |
| atgatgctat ggctggaagg aaagctgcct gttccaaagg tcctgcactt tgaacggcat | 780 |
| gatggctgga gcaatctgct catgagtgag gccgatggcg tcctttgctc ggaagagtat | 840 |
| gaagatgaac aaagccctga aaagattatc gagctgtatg cggagtgcat caggctcttt | 900 |
| cactccatcg acatatcgga ttgtccctat acgaatagct tagacagccg cttagccgaa | 960 |
| ttggattact tactgaataa cgatctggcc gatgtggatt gcgaaaactg ggaagaagac | 1020 |
| actccattta agatccgcg cgagctgtat gatttttaa agacggaaaa gcccgaagag | 1080 |
| gaacttgtct ttcccacgg cgacctggga gacagcaaca tctttgtgaa agatggcaaa | 1140 |
| gtaagtggct ttattgatct tgggagaagc ggcagggcgg acaagtggta tgacattgcc | 1200 | ttctgcgtcc ggtcgatcag ggaggatatc ggggaagaac agtatgtcga gctattttt   1260 gacttactgg ggatcaagcc tgattgggag aaaataaaat attatatttt actggatgaa   1320 ttgttttagt acctagattt agatgtctaa aaagctttaa ctacaagctt tttagacatc   1380 taatcttttc tgaagtacat ccgcaactgt ccatactctg atgttttata tcttttctaa   1440 aagttcgcta gataggggtc ccgagcgcct acgaggaatt tgtatcgat              1489

<210> SEQ ID NO 12
<211> LENGTH: 20
<212> TYPE: DNA
<213> ORGANISM: Artificial Sequence
<220> FEATURE:
<223> OTHER INFORMATION: primer slr0168up-R

<400> SEQUENCE: 12
taccgttcaa attctgtggg                                              20

<210> SEQ ID NO 13
<211> LENGTH: 36
<212> TYPE: DNA
<213> ORGANISM: Artificial Sequence
<220> FEATURE:
<223> OTHER INFORMATION: primer slr0168up/Pcpc560-F

<400> SEQUENCE: 13
agaatttgaa cggtaacctg tagagaagag tccctg                            36

<210> SEQ ID NO 14
<211> LENGTH: 21
<212> TYPE: DNA
<213> ORGANISM: Artificial Sequence
<220> FEATURE:
<223> OTHER INFORMATION: primer Pcpc560-R

<400> SEQUENCE: 14
tgaattaatc tcctacttga c                                            21

<210> SEQ ID NO 15
<211> LENGTH: 560
<212> TYPE: DNA
<213> ORGANISM: Synechocystis sp. PCC6803

<400> SEQUENCE: 15
acctgtagag aagagtccct gaatatcaaa atggtgggat aaaaagctca aaaggaaag    60 taggctgtgg ttccctaggc aacagtcttc cctaccccac tggaaactaa aaaacgaga   120 aaagttcgca ccgaacatca attgcataat tttagcccta aaacataagc tgaacgaaac  180
tggttgtctt cccttcccaa tccaggacaa tctgagaatc ccctgcaaca ttacttaaca  240
aaaaagcagg aataaaatta acaagatgta acagacataa gtcccatcac cgttgtataa  300
agttaactgt gggattgcaa agcattcaa gcctaggcgc tgagctgttt gagcatcccg   360
gtggcccttg tcgctgcctc cgtgtttctc cctggattta tttaggtaat atctctcata  420
aatccccggg tagttaacga aagttaatgg agatcagtaa caataactct agggtcatta  480
ctttggactc cctcagtta tccgggggaa ttgtgtttaa gaaatccca actcataaag    540 tcaagtagga gattaattca                                              560

<210> SEQ ID NO 16
<211> LENGTH: 20
<212> TYPE: DNA

```
<213> ORGANISM: Artificial Sequence
<220> FEATURE:
<223> OTHER INFORMATION: primer Trbc-F

<400> SEQUENCE: 16
gttacagttt tggcaattac                                                 20

<210> SEQ ID NO 17
<211> LENGTH: 38
<212> TYPE: DNA
<213> ORGANISM: Artificial Sequence
<220> FEATURE:
<223> OTHER INFORMATION: primer Km/Trbc-R

<400> SEQUENCE: 17
ttcgctgggt ttatcttccc cacttagata aaaaatcc                             38

<210> SEQ ID NO 18
<211> LENGTH: 183
<212> TYPE: DNA
<213> ORGANISM: Synechocystis sp. PCC6803

<400> SEQUENCE: 18
gttacagttt tggcaattac taaaaaactg acttcaattc aatgttagcc cgctcccgcg     60
ggttttttgt tgcttttttca cagtgactat aggtaatcag caacacaata cggccctgtt   120
ctttggacag ttttttgtata atgttgaccg catcctgacc ggattttttta tctaagtggg  180 gaa                                                                  183

<210> SEQ ID NO 19
<211> LENGTH: 36
<212> TYPE: DNA
<213> ORGANISM: Artificial Sequence
<220> FEATURE:
<223> OTHER INFORMATION: primer Pcpc560/NoKASII-F

<400> SEQUENCE: 19
taggagatta attcaatgat ggagaagctg accctc                               36

<210> SEQ ID NO 20
<211> LENGTH: 40
<212> TYPE: DNA
<213> ORGANISM: Artificial Sequence
<220> FEATURE:
<223> OTHER INFORMATION: primer Trbc/NoKASII-R

<400> SEQUENCE: 20
tgccaaaact gtaacctagg caacatactt cttgaagacc                           40

<210> SEQ ID NO 21
<211> LENGTH: 37
<212> TYPE: DNA
<213> ORGANISM: Artificial Sequence
<220> FEATURE:
<223> OTHER INFORMATION: primer Pcpc560/NoKASII(-40)-F

<400> SEQUENCE: 21
taggagatta attcaatgac tgtgcgtcgt gcatcag                              37

<210> SEQ ID NO 22
<211> LENGTH: 35
<212> TYPE: DNA
<213> ORGANISM: Artificial Sequence
<220> FEATURE:
<223> OTHER INFORMATION: primer Pcpc560/AtKASII-F
```

<400> SEQUENCE: 22

| taggagatta attcaatggt gggtgcgtct tcctc | 35 |

<210> SEQ ID NO 23
<211> LENGTH: 41
<212> TYPE: DNA
<213> ORGANISM: Artificial Sequence
<220> FEATURE:
<223> OTHER INFORMATION: primer Trbc/AtKASII-R

<400> SEQUENCE: 23

| tgccaaaact gtaactcact tgtaaggagc aaaaatgatg c | 41 |

<210> SEQ ID NO 24
<211> LENGTH: 1626
<212> TYPE: DNA
<213> ORGANISM: Arabidopsis thaliana

<400> SEQUENCE: 24

| atggtgggtg cgtcttcctc ttacgcatct ccgttatgta cctggtttgt tgctgcttgc | 60 |
| atgtccgtct ctcacggtgg aggagatagc cgtcaggctg ttgctcttca atctggtggg | 120 |
| cggagtcggc gaaggaggca gcttagcaaa tgctctgtcg cttctggatc cgctagcatt | 180 |
| caggctctcg tcacttcttg tttggatttt ggtccttgta ctcactacaa caacaacaat | 240 |
| gcattgtctt ctctctttgg atcgaatagt gtttctttga atcgaaacca gaggagattg | 300 |
| aatcgtgctg ctagctccgg tggagccatg cagtgatgg agatggaaaa ggaagctgcg | 360 |
| gttaacaaga aaccacctac ggagcagcgt cgagttgtag tgacaggcat gggagttgaa | 420 |
| acatcattgg tcatgacccc atataccttc tatgagaatt tgctacaagg caacagtggt | 480 |
| attagccaga ttgaaaattt tgattgttct gaatttccta cgcgaattgc gggagagatc | 540 |
| aaaagcttct cgactgaagg atgggttgct ccaaaacttt ctaaaaggat ggacaaattc | 600 |
| atgctctatc ttctcacagc tggtaagaaa gctttggctg atggtggggt tactgatgaa | 660 |
| gtaatggcag agtttgacaa aaccaaatgt ggagttttga ttggctcggc aatgggagga | 720 |
| atgaaggtct tttacgatgc tattgaagct ctgagaatcc cttacaagaa gatgaatcct | 780 |
| ttttgtgtac ctttttgcga acaaacatg ggttctgcta tgcttgccat ggatctggga | 840 |
| tggatggggc caactattc tatttcaact gcttgtgcca caagcaactt ttgcattctg | 900 |
| aattcagcaa accacattat taaaggtgaa gctgatgtaa tgctctgtgg tggctcagat | 960 |
| gcagttatta ttccaatagg gttgggaggt tttgttgcat gccgggctct tcacaaagg | 1020 |
| aataatgatc ccacaaaagc ttcacgtcct tgggatacca atcgagatgg tttcgtgatg | 1080 |
| ggagagggag ctggagttct acttttggaa gaactcgagc atgctaagaa agagggtgca | 1140 |
| actatctacg cagagttcct cggtgggagt ttcacatgtg atgcctatca catgaccgag | 1200 |
| cctcaccctg atgggctgg tgttattctc tgtattgaga gagcgttagc tagtgctggg | 1260 |
| atttccaagg aacaaataaa ttacataaat gcacatgcaa cctcaacgca tgctggagat | 1320 |
| attaaggaat accaagccct tgctcactgt tttggccaaa atcctgagct taaggtaaat | 1380 |
| tccacaaaat ctatgattgg acacttgctg ggagctgctg gggccgtgga ggctgttgca | 1440 |
| actgtgcagg cgatacggac cggatgggtt catccaaata tcaacctcga gaatccagac | 1500 |
| agtggagtgg atacaaagct gctggtgggt cctaagaagg agagactgga cattaaagca | 1560 |
| gccttgtcaa attcattcgg gtttggtggt cataactcca gcatcatttt tgctccttac | 1620 | aagtga                                                                1626

<210> SEQ ID NO 25
<211> LENGTH: 36
<212> TYPE: DNA
<213> ORGANISM: Artificial Sequence
<220> FEATURE:
<223> OTHER INFORMATION: primer pUC118/NS1up-F

<400> SEQUENCE: 25
ggatcctcta gagtcaatgc cttctccaag ggcggc                                36

<210> SEQ ID NO 26
<211> LENGTH: 37
<212> TYPE: DNA
<213> ORGANISM: Artificial Sequence
<220> FEATURE:
<223> OTHER INFORMATION: primer Kmr/NS1up-R

<400> SEQUENCE: 26
ttcgctgggt ttatccttct ggagcaggaa gatgtcg                               37

<210> SEQ ID NO 27
<211> LENGTH: 798
<212> TYPE: DNA
<213> ORGANISM: Synechococcus elongatus sp.

<400> SEQUENCE: 27
aatgccttct ccaagggcgg cattcccctg actgttgaag gcgttgccaa tatcaagatt        60
gctggggaag aaccgaccat ccacaacgcg atcgagcggc tgcttggcaa aaaccgtaag       120
gaaatcgagc aaattgccaa ggagaccctc gaaggcaact tgcgtggtgt tttagccagc       180
ctcacgccgg agcagatcaa cgaggacaaa attgcctttg ccaaaagtct gctggaagag       240
gcggaggatg accttgagca gctgggtcaa gtcctcgata cgctgcaagt ccagaacatt       300
tccgatgagg tcggttatct ctcggctagt ggacgcaagc agcgggctga tctgcagcga       360
gatgcccgaa ttgctgaagc cgatgcccag gctgcctctg cgatccaaac ggccgaaaat       420
gacaagatca cggcccctgcg tcggatcgat cgcgatgtag cgatcgccca agccgaggcc       480
gagcgccgga ttcaggatgc gttgacgcgg cgcgaagcgg tggtggccga agctgaagcg       540
gacattgcta ccgaagtcgc tcgtagccaa gcagaactcc ctgtgcagca ggagcggatc       600
aaacaggtgc agcagcaact tcaagccgat gtgatcgccc cagctgaggc agcttgtaaa       660
cgggcgatcg cggaagcgcg gggggccgcc gcccgtatcg tcgaagatgg aaaagctcaa       720
gcggaaggga cccaacggct ggcggaggct tggcagaccg ctggtgctaa tgcccgcgac       780
atcttcctgc tccagaag                                                    798

<210> SEQ ID NO 28
<211> LENGTH: 36
<212> TYPE: DNA
<213> ORGANISM: Artificial Sequence
<220> FEATURE:
<223> OTHER INFORMATION: primer Kmr/NS1down-F

<400> SEQUENCE: 28
ggaatttgta tcgattcgag tccctgctcg tcacgc                                36

<210> SEQ ID NO 29
<211> LENGTH: 36
<212> TYPE: DNA
<213> ORGANISM: Artificial Sequence

```
<220> FEATURE:
<223> OTHER INFORMATION: primer pUC118/NS1down-R

<400> SEQUENCE: 29
gcatgcctgc aggtccggca tggcaatgtc tctctg                                36

<210> SEQ ID NO 30
<211> LENGTH: 781
<212> TYPE: DNA
<213> ORGANISM: Synechococcus elongatus sp.

<400> SEQUENCE: 30
tcgagtccct gctcgtcacg ctttcaggca ccgtgccaga tatcgacgtg gagtcgatca      60
ctgtgattgg cgaaggggaa ggcagcgcta cccaaatcgc tagcttgctg gagaagctga     120
aacaaaccac gggcattgat ctggcgaaat ccctaccggg tcaatccgac tcgcccgctg     180
cgaagtccta agagatagcg atgtgaccgc gatcgcttgt caagaatccc agtgatcccg     240
aaccatagga aggcaagctc aatgcttgcc tcgtcttgag gactatctag atgtctgtgg     300
aacgcacatt tattgccatc aagcccgatg gcgttcagcg gggtttggtc ggtacgatca     360
tcggccgctt tgagcaaaaa ggcttcaaac tggtgggcct aaagcagctg aagcccagtc     420
gcgagctggc cgaacagcac tatgctgtcc accgcgagcg ccccttcttc aatggcctcg     480
tcgagttcat cacctctggg ccgatcgtgg cgatcgtctt ggaaggcgaa ggcgttgtgg     540
cggctgctcg caagttgatc ggcgctacca atccgctgac ggcagaaccg gcaccatcc     600 gtggtgattt tggtgtcaat attggccgca acatcatcca tggctcggat gcaatcgaaa     660
cagcacaaca ggaaattgct ctctggttta gcccagcaga gctaagtgat tggaccccca     720
cgattcaacc ctggctgtac gaataaggtc tgcattcctt cagagagaca ttgccatgcc     780
g                                                                     781

<210> SEQ ID NO 31
<211> LENGTH: 21
<212> TYPE: DNA
<213> ORGANISM: Artificial Sequence
<220> FEATURE:
<223> OTHER INFORMATION: primer NS1down-F

<400> SEQUENCE: 31
tcgagtccct gctcgtcacg c                                                21

<210> SEQ ID NO 32
<211> LENGTH: 38
<212> TYPE: DNA
<213> ORGANISM: Artificial Sequence
<220> FEATURE:
<223> OTHER INFORMATION: primer Kmr/Ptrc-F

<400> SEQUENCE: 32
ggaatttgta tcgatttgac aattaatcat ccggctcg                              38

<210> SEQ ID NO 33
<211> LENGTH: 23
<212> TYPE: DNA
<213> ORGANISM: Artificial Sequence
<220> FEATURE:
<223> OTHER INFORMATION: primer Ptrc-R

<400> SEQUENCE: 33
ggtctgtttc ctgtgtgaaa ttg                                              23
```

<210> SEQ ID NO 34
<211> LENGTH: 74
<212> TYPE: DNA
<213> ORGANISM: Artificial Sequence
<220> FEATURE:
<223> OTHER INFORMATION: Ptrc fragment

<400> SEQUENCE: 34
ttgacaatta atcatccggc tcgtataatg tgtggaattg tgagcggata acaatttcac    60
acaggaaaca gacc                                                     74

<210> SEQ ID NO 35
<211> LENGTH: 38
<212> TYPE: DNA
<213> ORGANISM: Artificial Sequence
<220> FEATURE:
<223> OTHER INFORMATION: primer NS1down/Trbc-R

<400> SEQUENCE: 35
cgagcaggga ctcgattccc cacttagata aaaaatcc                           38

<210> SEQ ID NO 36
<211> LENGTH: 36
<212> TYPE: DNA
<213> ORGANISM: Artificial Sequence
<220> FEATURE:
<223> OTHER INFORMATION: primer Ptrc/NoKASII-F

<400> SEQUENCE: 36
cacaggaaac agaccatgat ggagaagctg accctc                             36

<210> SEQ ID NO 37
<211> LENGTH: 37
<212> TYPE: DNA
<213> ORGANISM: Artificial Sequence
<220> FEATURE:
<223> OTHER INFORMATION: primer Ptrc/NoKASII(-40)-F

<400> SEQUENCE: 37
cacaggaaac agaccatgac tgtgcgtcgt gcatcag                            37

<210> SEQ ID NO 38
<211> LENGTH: 35
<212> TYPE: DNA
<213> ORGANISM: Artificial Sequence
<220> FEATURE:
<223> OTHER INFORMATION: primer Ptrc/AtKASII-F

<400> SEQUENCE: 38
cacaggaaac agaccatggt gggtgcgtct tcctc                              35

<210> SEQ ID NO 39
<211> LENGTH: 39
<212> TYPE: DNA
<213> ORGANISM: Artificial Sequence
<220> FEATURE:
<223> OTHER INFORMATION: primer Ptrc/EcKASII-F

<400> SEQUENCE: 39
cacaggaaac agaccatgtc taagcgtcgt gtagttgtg                          39

<210> SEQ ID NO 40
<211> LENGTH: 42
<212> TYPE: DNA
<213> ORGANISM: Artificial Sequence
<220> FEATURE:
<223> OTHER INFORMATION: primer Trbc/EcKASII-R

<400> SEQUENCE: 40
tgccaaaact gtaacttaga tcttttaaa gatcaaagaa cc          42

<210> SEQ ID NO 41
<211> LENGTH: 1242
<212> TYPE: DNA
<213> ORGANISM: Escherichia coli

<400> SEQUENCE: 41
atgtctaagc gtcgtgtagt tgtgaccgga ctgggcatgt tgtctcctgt cggcaatacc       60
gtagagtcta cctggaaagc tctgcttgcc ggtcagagtg gcatcagcct aatcgaccat      120
ttcgatacta gcgcctatgc aacgaaattt gctggcttag taaaggattt taactgtgag      180
gacattatct cgcgcaaaga acagcgcaag atggatgcct tcattcaata tggaattgtc      240
gctggcgttc aggccatgca ggattctggc cttgaaataa cggaagagaa cgcaaccccg c    300 attggtgccg caattggctc cgggattggc ggcctcggac tgatcgaaga aaaccacaca      360
tctctgatga cgtggtgcc acgtaagatc agcccattct tcgttccgtc aacgattgtg       420
aacatggtgg caggtcatct gactatcatg tatggcctgc gtggcccgag catctctatc      480
gcgactgcct gtacttccgg cgtgcacaac attggccatg ctgcgcgtat tatcgcgtat      540
ggcgatgctg acgtgatggt tgcaggtggc gcagagaaag ccagtacgcc gctgggcgtt      600
ggtggttttg cgcggcacg tgcattatct acccgcaatg ataacccgca agcggcgagc       660
cgcccgtggg ataaagagcg tgatggtttc gtactgggcg atggtgccgg tatgctggta      720
cttgaagagt acgaacacgc gaaaaaacgc ggtgcgaaaa tttacgctga actcgtcggc      780
tttggtatga gcagcgatgc ttatcatatg acgtcaccgc cagaaaatgg cgcaggcgca      840
gctctggcga tggcaaatgc tctgcgtgat gcaggcattg aagcgagtca gattggctac      900
gttaacgcgc acggtacttc tacgccggct ggcgataaag ctgaagcgca ggcggtgaaa      960
accatcttcg gtgaagctgc aagccgtgtg ttggtaagct ccacgaaatc tatgaccggt     1020
cacctgttag gtgcggcggg tgcagtagaa tctatctact ccatcctggc gctgcgcgat     1080
caggctgttc cgccaaccat caacctggat aacccggatg aaggttgcga tctggatttc     1140
gtaccgcacg aagcgcgtca ggttagcgga atggaataca ctctgtgtaa ctccttcggc     1200
ttcggtggca ctaatggttc tttgatcttt aaaaagatct aa                         1242

<210> SEQ ID NO 42
<211> LENGTH: 541
<212> TYPE: PRT
<213> ORGANISM: Arabidopsis thaliana

<400> SEQUENCE: 42

Met Val Gly Ala Ser Ser Tyr Ala Ser Pro Leu Cys Thr Trp Phe
1               5                   10                  15

Val Ala Ala Cys Met Ser Val Ser His Gly Gly Gly Asp Ser Arg Gln
                20                  25                  30

Ala Val Ala Leu Gln Ser Gly Arg Ser Arg Arg Arg Gln Leu
            35                  40                  45

Ser Lys Cys Ser Val Ala Ser Gly Ser Ala Ser Ile Gln Ala Leu Val
        50                  55                  60

Thr Ser Cys Leu Asp Phe Gly Pro Cys Thr His Tyr Asn Asn Asn Asn
65                  70                  75                  80

```
Ala Leu Ser Ser Leu Phe Gly Ser Asn Ser Val Ser Leu Asn Arg Asn
                85                  90                  95

Gln Arg Arg Leu Asn Arg Ala Ala Ser Ser Gly Gly Ala Met Ala Val
            100                 105                 110

Met Glu Met Glu Lys Glu Ala Ala Val Asn Lys Lys Pro Pro Thr Glu
        115                 120                 125

Gln Arg Arg Val Val Val Thr Gly Met Gly Val Glu Thr Ser Leu Gly
    130                 135                 140

His Asp Pro His Thr Phe Tyr Glu Asn Leu Leu Gln Gly Asn Ser Gly
145                 150                 155                 160

Ile Ser Gln Ile Glu Asn Phe Asp Cys Ser Glu Phe Pro Thr Arg Ile
                165                 170                 175

Ala Gly Glu Ile Lys Ser Phe Ser Thr Glu Gly Trp Val Ala Pro Lys
            180                 185                 190

Leu Ser Lys Arg Met Asp Lys Phe Met Leu Tyr Leu Thr Ala Gly
        195                 200                 205

Lys Lys Ala Leu Ala Asp Gly Gly Val Thr Asp Glu Val Met Ala Glu
    210                 215                 220

Phe Asp Lys Thr Lys Cys Gly Val Leu Ile Gly Ser Ala Met Gly Gly
225                 230                 235                 240

Met Lys Val Phe Tyr Asp Ala Ile Glu Ala Leu Arg Ile Ser Tyr Lys
                245                 250                 255

Lys Met Asn Pro Phe Cys Val Pro Phe Ala Thr Thr Asn Met Gly Ser
            260                 265                 270

Ala Met Leu Ala Met Asp Leu Gly Trp Met Gly Pro Asn Tyr Ser Ile
        275                 280                 285

Ser Thr Ala Cys Ala Thr Ser Asn Phe Cys Ile Leu Asn Ser Ala Asn
    290                 295                 300

His Ile Ile Lys Gly Glu Ala Asp Val Met Leu Cys Gly Gly Ser Asp
305                 310                 315                 320

Ala Val Ile Ile Pro Ile Gly Leu Gly Gly Phe Val Ala Cys Arg Ala
                325                 330                 335

Leu Ser Gln Arg Asn Asn Asp Pro Thr Lys Ala Ser Arg Pro Trp Asp
            340                 345                 350

Thr Asn Arg Asp Gly Phe Val Met Gly Glu Gly Ala Gly Val Leu Leu
        355                 360                 365

Leu Glu Glu Leu Glu His Ala Lys Lys Arg Gly Ala Thr Ile Tyr Ala
    370                 375                 380

Glu Phe Leu Gly Gly Ser Phe Thr Cys Asp Ala Tyr His Met Thr Glu
385                 390                 395                 400

Pro His Pro Asp Gly Ala Gly Val Ile Leu Cys Ile Glu Arg Ala Leu
                405                 410                 415

Ala Ser Ala Gly Ile Ser Lys Glu Gln Ile Asn Tyr Ile Asn Ala His
            420                 425                 430

Ala Thr Ser Thr His Ala Gly Asp Ile Lys Glu Tyr Gln Ala Leu Ala
        435                 440                 445

His Cys Phe Gly Gln Asn Pro Glu Leu Lys Val Asn Ser Thr Lys Ser
    450                 455                 460

Met Ile Gly His Leu Leu Gly Ala Ala Gly Ala Val Glu Ala Val Ala
465                 470                 475                 480

Thr Val Gln Ala Ile Arg Thr Gly Trp Val His Pro Asn Ile Asn Leu
                485                 490                 495
```

-continued

Glu Asn Pro Asp Ser Gly Val Asp Thr Lys Leu Leu Val Gly Pro Lys
            500                 505                 510

Lys Glu Arg Leu Asp Ile Lys Ala Ala Leu Ser Asn Ser Phe Gly Phe
        515                 520                 525

Gly Gly His Asn Ser Ser Ile Ile Phe Ala Pro Tyr Lys
    530                 535                 540

<210> SEQ ID NO 43
<211> LENGTH: 413
<212> TYPE: PRT
<213> ORGANISM: Escherichia coli

<400> SEQUENCE: 43

Met Ser Lys Arg Arg Val Val Thr Gly Leu Gly Met Leu Ser Pro
1               5                   10                  15

Val Gly Asn Thr Val Glu Ser Thr Trp Lys Ala Leu Leu Ala Gly Gln
            20                  25                  30

Ser Gly Ile Ser Leu Ile Asp His Phe Asp Thr Ser Ala Tyr Ala Thr
        35                  40                  45

Lys Phe Ala Gly Leu Val Lys Asp Phe Asn Cys Glu Asp Ile Ile Ser
    50                  55                  60

Arg Lys Glu Gln Arg Lys Met Asp Ala Phe Ile Gln Tyr Gly Ile Val
65                  70                  75                  80

Ala Gly Val Gln Ala Met Gln Asp Ser Gly Leu Glu Ile Thr Glu Glu
                85                  90                  95

Asn Ala Thr Arg Ile Gly Ala Ala Ile Gly Ser Gly Ile Gly Gly Leu
            100                 105                 110

Gly Leu Ile Glu Glu Asn His Thr Ser Leu Met Asn Gly Gly Pro Arg
        115                 120                 125

Lys Ile Ser Pro Phe Phe Val Pro Ser Thr Ile Val Asn Met Val Ala
    130                 135                 140

Gly His Leu Thr Ile Met Tyr Gly Leu Arg Gly Pro Ser Ile Ser Ile
145                 150                 155                 160

Ala Thr Ala Cys Thr Ser Gly Val His Asn Ile Gly His Ala Ala Arg
                165                 170                 175

Ile Ile Ala Tyr Gly Asp Ala Asp Val Met Val Ala Gly Gly Ala Glu
            180                 185                 190

Lys Ala Ser Thr Pro Leu Gly Val Gly Gly Phe Gly Ala Ala Arg Ala
        195                 200                 205

Leu Ser Thr Arg Asn Asp Asn Pro Gln Ala Ala Ser Arg Pro Trp Asp
    210                 215                 220

Lys Glu Arg Asp Gly Phe Val Leu Gly Asp Gly Ala Gly Met Leu Val
225                 230                 235                 240

Leu Glu Glu Tyr Glu His Ala Lys Lys Arg Gly Ala Lys Ile Tyr Ala
                245                 250                 255

Glu Leu Val Gly Phe Gly Met Ser Ser Asp Ala Tyr His Met Thr Ser
            260                 265                 270

Pro Pro Glu Asn Gly Ala Gly Ala Ala Leu Ala Met Ala Asn Ala Leu
        275                 280                 285

Arg Asp Ala Gly Ile Glu Ala Ser Gln Ile Gly Tyr Val Asn Ala His
    290                 295                 300

Gly Thr Ser Thr Pro Ala Gly Asp Lys Ala Glu Ala Gln Ala Val Lys
305                 310                 315                 320

Thr Ile Phe Gly Glu Ala Ala Ser Arg Val Leu Val Ser Ser Thr Lys
                325                 330                 335

-continued

```
Ser Met Thr Gly His Leu Leu Gly Ala Ala Gly Ala Val Glu Ser Ile
            340                 345                 350

Tyr Ser Ile Leu Ala Leu Arg Asp Gln Ala Val Pro Pro Thr Ile Asn
        355                 360                 365

Leu Asp Asn Pro Asp Glu Gly Cys Asp Leu Asp Phe Val Pro His Glu
370                 375                 380

Ala Arg Gln Val Ser Gly Met Glu Tyr Thr Leu Cys Asn Ser Phe Gly
385                 390                 395                 400

Phe Gly Gly Thr Asn Gly Ser Leu Ile Phe Lys Lys Ile
                405                 410

<210> SEQ ID NO 44
<211> LENGTH: 436
<212> TYPE: PRT
<213> ORGANISM: Nannochloropsis oculata

<400> SEQUENCE: 44

Met Thr Val Arg Arg Ala Ser Gly Glu Val Ser Met Ala Asp Leu Pro
1               5                   10                  15

Pro Leu Val Arg Lys Arg Val Val Ile Thr Gly Val Gly Ala Val Ser
            20                  25                  30

Pro Leu Gly Trp Gly Asp Asp Phe Trp Asn Gly Leu Val Glu Gly Arg
        35                  40                  45

Ser Gly Ile Val Arg Leu Pro Ser Trp Ala Asp Glu Tyr Pro Ala Arg
    50                  55                  60

Ile Gly Gly Leu Val Pro Asp His Phe Lys Pro Ser Asp Tyr Met Asn
65                  70                  75                  80

Ala Lys Glu Val Lys Arg Gln Ala Arg Phe Thr His Phe Ala Met Ala
                85                  90                  95

Ala Ala Arg Met Ala Val Glu Asp Ala Lys Leu Asp Leu Glu Lys Val
            100                 105                 110

Asp Arg Ser Arg Ala Gly Cys Met Ile Gly Ser Gly Ile Gly Gly Val
        115                 120                 125

Glu Ile Phe Glu Lys Asn Cys Gly Glu Phe Asp Lys Lys Gly Gly Gly
    130                 135                 140

Leu Pro Gly Leu Lys Ala Val Ser Pro Phe Leu Ile Pro Ala Leu Ile
145                 150                 155                 160

Ala Asn Thr Ala Ala Gly Thr Val Ala Ile Glu Leu Gly Leu Lys Gly
                165                 170                 175

Pro Asn Tyr Cys Ser Val Ser Ala Cys Ala Ser Gly Thr His Thr Ile
            180                 185                 190

Gly Asp Ala Phe Phe Phe Leu Gln Asn Gly Met Ala Asp Val Cys Val
        195                 200                 205

Thr Gly Gly Thr Glu Ala Ala Ile Thr Pro Leu Cys Phe Ala Gly Phe
    210                 215                 220

Val Ala Ile Arg Ala Leu Thr Thr Ser Gly Asn Asp Asp Pro Thr Lys
225                 230                 235                 240

Ala Ser Lys Pro Phe Asp Lys Asn Arg Ala Gly Phe Val Met Ala Glu
                245                 250                 255

Gly Ala Gly Met Leu Val Leu Glu Thr Glu Glu His Ala Lys Ala Arg
            260                 265                 270

Gly Ala Thr Ile Tyr Ala Glu Leu Ala Gly Tyr Gly Ala Ser Cys Asp
        275                 280                 285

Ala His His Ile Thr Ala Pro His Pro Glu Gly Glu Gly Leu Ala Asn
```

```
                    290             295             300
Ala Met Asn Met Ala Leu Thr Ser Ala Gly Leu Lys Pro Thr Asp Val
305                 310             315                 320

Asp Tyr Ile Asn Ala His Gly Thr Ser Thr Ala Tyr Asn Asp Lys Phe
                325             330             335

Glu Thr Leu Ala Ile His Arg Val Phe Gly Glu His Ala Lys Lys Leu
                340             345             350

Lys Val Ser Ser Ile Lys Ser Met Thr Gly His Ser Leu Gly Ala Ala
            355             360             365

Gly Ala Phe Glu Ala Val Ala Cys Ala Lys Ala Ile Lys Glu Gly Ile
        370             375             380

Ile Pro Pro Thr Ile Asn Tyr Glu Thr Pro Asp Pro Asp Cys Asp Leu
385             390             395                 400

Asp Tyr Val Pro Asn Lys Ala Ile Lys His Asp Val Asn Val Ala Ile
                405             410             415

Ser Asp Asn Leu Gly Phe Gly Gly His Asn Ala Ala Leu Val Phe Lys
            420             425             430

Lys Tyr Val Ala
        435

<210> SEQ ID NO 45
<211> LENGTH: 1311
<212> TYPE: DNA
<213> ORGANISM: Nannochloropsis oculata

<400> SEQUENCE: 45
atgactgtgc gtcgtgcatc aggggaagtg agcatggcgg acttgccccc gcttgtccgc      60
aagagggtgg tgatcacggg tgtcggcgcc gtgtctcctc tcgggtgggg agacgacttc     120
tggaacggtc tcgtggaggg aaggagcggc attgtccgcc tcccttcgtg gcggacgag      180 tacccgcgcg aatcggagg cttggtcccg gatcacttta agccgagcga ctacatgaat      240
gccaaggagg tgaaacgaca ggcccgcttc acccattttg ccatggcagc tgcccgtatg     300
gccgtggaag acgccaagct cgacctggag aaggtggacc gctcgcgtgc cgggtgcatg     360
ataggatccg gcattggtgg tgtagaaatc ttcgagaaaa actgtgggga attcgacaag     420
aagggcggag ggctccctgg cctcaaggct gtctccccct tcctgattcc ggccctcatc     480
gccaacaccg cagccgggac agtggctatt gaactcggct tgaagggccc gaactactgc     540
tctgtctccg cctgcgcctc gggcacgcat accatcggtg atgccttctt cttcctccaa     600
aacggcatgg cggacgtttg tgtaacgggc gggacggaag ccgccatcac ccccctctgt     660
tttgcgggat tgtcgccat cgcgcccctt accaccagtg caacgacga ccccaccaag     720 gcctccaagc cgttcgacaa gaaccgagcc ggtttcgtta tggccgaggg agcggggatg     780
ctcgtccttg agacggagga acacgcgaag gcccgaggtg ccaccatcta tgccgagctt     840
gctggctacg gcgcatcctg cgacgcccac cacatcaccg cccccatcc cgaaggcgag     900 gggctggcga acgcgatgaa tatggctctg acgtccgccg gcctcaagcc tacgacgtg     960 gactacatta tgcccatgg aaccagcacg gcctacaacg acaaattcga gacgctggcc    1020
attcaccgcg tctttggcga gcacgccaag aagctgaagg tttcttccat caagtcaatg    1080
actggtcact ccctcgggc gccggtgcc ttcgaggccg tggcgtgcgc gaaggcaatc    1140
aaggagggca tcatcccgcc caccatcaac tacgagactc ccgatccaga ctgcgacttg    1200
```

```
gactatgttc ccaacaaggc gatcaagcac gacgtgaatg tggccatctc cgataacctg    1260
ggcttcggcg ggcacaacgc ggctttggtc ttcaagaagt atgttgccta g             1311
```

METHOD OF PRODUCING LIPID

TECHNICAL FIELD

The present invention relates to a method of producing lipids. Further, the present invention also relates to a transformant for use in this method.

BACKGROUND ART

Fatty acids are one of the principal components of lipids. In vivo, fatty acids are bonded to glycerin via an ester bond to form lipids (fats and oils) such as triacylglycerol. Further, many animals and plants also store and utilize fatty acids as an energy source. These fatty acids and lipids stored in animals and plants are widely utilized for food or industrial use.

For example, higher alcohol derivatives that are obtained by reducing higher fatty acids having approximately 12 to 18 carbon atoms are used as surfactants. Alkyl sulfuric acid ester salts, alkyl benzene sulfonic acid salts and the like are utilized as anionic surfactants. Further, polyoxyalkylene alkyl ethers, alkyl polyglycosides and the like are utilized as nonionic surfactants. These surfactants are used for detergents, disinfectants, or the like. Cationic surfactants such as alkylamine salts and mono- or dialkyl-quaternary ammonium salts, as other higher alcohol derivatives, are commonly used for fiber treatment agents, hair conditioning agents, disinfectants, or the like. Further, benzalkonium type quaternary ammonium salts are commonly used for disinfectants, antiseptics, or the like. Furthermore, vegetable fats and oils are also used as raw materials of biodiesel fuels.

Further, long-chain fatty acids having 20 or more carbon atoms are different in chemical properties depending on a degree of unsaturation, and used in various applications. For example, long-chain polyunsaturated fatty acids such as EPA (eicosapentaenoic acid) and DHA (docosahexaenoic acid) are used as a physiologically functional food. Further, long-chain saturated fatty acids or long-chain monounsaturated fatty acids, such as arachidic acid, behenic acid and erucic acid, are useful as an industrial raw material for a dispersing agent, a lubricating oil, or the like.

Generally, a fatty acid synthetic pathway of plants is localized in the chloroplast. In the chloroplast, an elongation reaction of the carbon chain is repeated starting from an acetyl-CoA and a malonyl-ACP (acyl-carrier-protein), and finally an acyl-ACP (a composite consisting of an acyl group being a fatty acid residue and an ACP. Here, the number of carbon atoms indicates the number of carbon atoms of the acyl group, and indicates the same hereinafter in several cases) having 16 or 18 carbon atoms is synthesized. A β-ketoacyl-acyl-carrier-protein synthase (hereinafter, also referred to as "KAS") is an enzyme involved in control of chain length of the acyl group, among enzymes involved in the fatty acid synthetic pathway. In plants, four kinds of KASs having different function respectively, namely KAS I, KAS II, KAS III and KAS IV are known to exist. Among these, KAS III functions in a stage of starting a chain length elongation reaction to elongate the acetyl-CoA having 2 carbon atoms to the β-ketoacyl-ACP having 4 carbon atoms. In the subsequent elongation reaction, KAS I, KAS II and KAS IV are involved. KAS I is mainly involved in the elongation reaction to the palmitoyl-ACP having 16 carbon atoms, and KAS II is mainly involved in the elongation reaction to the stearoyl-ACP having 18 carbon atoms. On the other hand, it is believed that KAS IV is involved in the elongation reaction to medium-chain acyl-ACP having 6 to 14 carbon atoms.

Among them, Patent Literature 1 describes, as KAS II, KAS II of algae belonging to genus *Nannochloropsis* being one kind of algae.

As mentioned above, fatty acids are widely used in various applications. Therefore, attempts have been made on improving productivity of the fatty acids or the lipids in vivo by using hosts such as plants or bacteria. Furthermore, applications and usefulness of the fatty acids depend on the number of carbon atoms (chain length) or unsaturated bonds (degree of unsaturation) thereof. Therefore attempts have been made also on controlling the number of carbon atoms or unsaturated bonds of the fatty acids.

Cyanobacteria (blue-green bacteria) belong to a group of eubacteria, and have an ability to produce oxygen through photosynthesis and fix carbon dioxide. More than billion years ago, cyanobacteria were engulfed by eukaryotic cells. Such intracellular symbiont (primary symbiosis), cyanobacteria, are considered as an origin of chloroplasts. Thus cyanobacteria have been widely used in photosynthesis studies as an ancestor organism of chloroplasts. Further, cyanobacteria grow faster than other plants, and have high photosynthetic ability. Furthermore, cyanobacteria also have a transformation ability.

Because of this, cyanobacteria, to which foreign DNA is introduced in the cells, can be used in microbiological production of substances, and thus have attracted attention as a host for producing substances such as biofuel.

As examples of producing substances using cyanobacteria, production of fatty acids has been reported (Patent Literature 2 and Non-Patent Literature 1). However, almost no studies have reported on attempts of producing the long-chain fatty acids having 20 or more carbon atoms by using the cyanobacteria.

CITATION LIST

Patent Literatures

Patent Literature 1: US 2013/0102040
Patent Literature 2: WO 2009/076559

NON-PATENT LITERATURES

Non-Patent Literature 1: Proc. Natl. Acad. Sci. USA, 2011, vol. 108, p. 6899-6904

SUMMARY OF INVENTION

The present invention relates to a method of producing lipids, containing the steps of:
culturing a transformant wherein the expression of a gene encoding at least any one of the following proteins (A) to (D) is enhanced in a cyanobacteria cell, and
producing fatty acids or lipids containing these fatty acids as components:
(A) a protein consisting of the amino acid sequence set forth in SEQ ID NO: 1;
(B) a protein consisting of an amino acid sequence having 60% or more identity with the amino acid sequence of the protein (A), and having β-ketoacyl-ACP synthase activity (hereinafter, also referred to as "KAS activity");
(C) a protein consisting of the amino acid sequence set forth in SEQ ID NQ: 44; and (D) a protein consisting of an amino acid sequence having 60% or more identity with the amino acid sequence of the protein (C), and having KAS activity.

Further, the present invention relates to a method of improving lipid productivity, containing the steps of: enhancing the expression of a gene encoding at least any one of the proteins (A) to (D) in a cyanobacteria cell, and improving the productivity of long-chain fatty acids or the lipids containing these fatty acids as components, produced in a cyanobacteria cell.

Further, the present invention relates to a method of modifying the composition of lipids, containing the steps of: enhancing the gene expression of a gene encoding at least any one of the proteins (A) to (D) in a cyanobacteria cell, and improving the productivity of long-chain fatty acids or the lipids containing these fatty acids as components produced in a cyanobacteria cell, to modify the composition of fatty acids or lipids in all fatty acids or all lipids to be produced.

Further, the present invention relates to a method of providing an ability to produce long-chain fatty acids or the lipids containing these fatty acids as components with cyanobacteria, containing the step of enhancing the gene expression of a gene encoding at least any one of the proteins (A) to (D) in a cyanobacteria cell.

Furthermore, the present invention relates to a transformant, wherein the expression of a gene encoding at least any one of the proteins (A) to (D) is enhanced in a cyanobacteria cell.

Other and further features and advantages of the invention will appear more fully from the following description.

MODE FOR CARRYING OUT THE INVENTION

The present invention relates to a method of producing lipids using a cyanobacteria, which improves productivity of long-chain fatty acids or the lipids containing these fatty acids as components.

Further, the present invention relates to a transformant of cyanobacteria in which the productivity of long-chain fatty acids or the lipids containing these fatty acids as components is improved.

The present inventors focused attention on KAS of algae belonging to the genus *Nannochloropsis* as an enzyme involved in synthesis of the long-chain fatty acids, and expression of a gene encoding this KAS of algae belonging to the genus *Nannochloropsis* was enhanced within cells of the cyanobacteria. As a result, the present inventors found that the cyanobacteria, originally having no ability to produce the long-chain fatty acids, acquire the ability to produce the long-chain fatty acids. Further, the present inventors found that the ability to produce the long-chain fatty acids is improved in comparison with a case where the expression of the gene encoding the KAS of algae belonging to the genus *Nannochloropsis* is not enhanced.

The present invention was completed based on these findings.

According to the method of producing the lipids of the present invention, the productivity of long-chain fatty acids or the lipids containing these fatty acids as components can be improved.

Moreover, the transformant of the present invention is excellent in the productivity of long-chain fatty acids or the lipids containing these fatty acids as components.

The term "lipid(s)" in the present specification, covers a simple lipid such as a neutral lipid (triacylglycerol, or the like), wax, and a ceramide; a complex lipid such as a phospholipid, a glycolipid, and a sulfolipid; and a derived lipid obtained from the lipid such as a fatty acid (free fatty acid), alcohols, and hydrocarbons.

The fatty acids categorized into the derived lipid generally refer to the fatty acids per se and mean "free fatty acids". In the present invention, a part of the fatty acids or a part of the acyl group in molecules of a simple lipid and a complex lipid is expressed as "fatty acid residue". Then, unless otherwise specified, a term "fatty acid" is used as a generic term for "free fatty acid" and "fatty acid residue".

Moreover, a term "fatty acids or lipids containing these fatty acids as components" in the present specification is generically used including "free fatty acids" and "lipids having the fatty acid residues". Further, a term "fatty acid composition" in the present specification means a weight proportion of each fatty acid relative to the weight of whole fatty acids (total fatty acids) obtained by totaling the free fatty acids and the fatty acid residues described above. The weight (production amount) of the fatty acids or the fatty acid composition can be measured according to the method used in Examples.

In the present specification, the description of "Cx:y" for the fatty acid or the acyl group constituting the fatty acid means that the number of carbon atoms is "x" and the number of double bonds is "y". The description of "Cx" means a fatty acid or an acyl group having "x" as the number of carbon atoms.

In the present specification, the identity of the nucleotide sequence and the amino acid sequence is calculated through the Lipman-Pearson method (Science, 1985, vol. 227, p. 1435-1441). Specifically, the identity can be determined through use of a homology analysis (search homology) program of genetic information processing software Genetyx-Win with Unit size to compare (ktup) being set to 2.

It should be note that, in this description, the "stringent conditions" includes, for example, the method described in Molecular Cloning—A LABORATORY MANUAL THIRD EDITION [Joseph Sambrook, David W. Russell, Cold Spring Harbor Laboratory Press], and examples thereof include conditions where hybridization is performed by incubating a solution containing 6×SSC (composition of 1×SSC: 0.15 M sodium chloride, 0.015 M sodium citrate, pH7.0), 0.5% SDS, 5×Denhardt and 100 mg/mL herring sperm DNA together with a probe at 65° C. for 8 to 16 hours.

Furthermore, in the present specification, the term "upstream" of a gene means a region subsequent to a 5' side of a targeted gene or region, and not a position from a translational initiation site. On the other hand, the term "downstream" of the gene means a region subsequent to a 3' side of the targeted gene or region.

The above-described protein (A) to (D) (hereinafter, also referred to as "NoKASII") is one of the KAS, and the protein involved in a long-chain fatty acid synthesis. The protein consisting of the amino acid sequence set forth in SEQ ID NO: 1 is one of the KAS derived from *Nannochioropsis oculata* NIES-2145 being algae belonged to the genus *Nannochioropsis*.

The KAS is an enzyme involved in control of chain length of an acyl group in the fatty acid synthetic pathway. The fatty acid synthetic pathway of plants is generally localized in the chloroplast. In the chloroplast, the elongation reaction of the carbon chain is repeated starting from an acetyl-CoA, and finally an acyl-ACP having 16 or 18 carbon atoms is synthesized. Then, an acyl-ACP thioesterase (hereinafter, also merely referred to as "TE") hydrolyzes the thioester bond of the acyl-ACP to form a free fatty acid.

In the first stage of the fatty acid synthesis, an acetoacetyl-ACP is formed by a condensation reaction between the acetyl-CoA and a malonyl-ACP. The KAS catalyzes this reaction. Then, the keto group of the acetoacetyl-ACP is reduced by a β-ketoacyl-ACP reductase, to produce a hydroxybutyryl-ACP. Subsequently, the hydroxybutyryl-ACP is dehydrated by a β-hydroxyacyl-ACP dehydrase, to produce a crotonyl-ACP. Finally, the crotonyl-ACP is reduced by an enoyl-ACP reductase, to produce a butyryl-ACP. The butyryl-ACP in which two carbon atoms are added to the carbon chain of the acyl group of the acetyl-ACP is produced by a series of these reactions. Hereinafter, the similar reactions are repeated to cause elongation of the carbon chain of the acyl-ACP, and an acyl-ACP having 16 or 18 carbon atoms is finally synthesized.

The proteins (A) to (D) described above have the KAS activity. In the present specification, the term "KAS activity" means the activity to catalyze the condensation reaction of the acetyl-CoA or the acyl-ACP with the malonyl-ACP.

The KAS activity of the protein can be confirmed by, for example, introducing a DNA produced by linking a gene encoding the protein to the downstream of a promoter which functions in a host cell, into a host cell which lacks a fatty acid degradation system, culturing the thus-obtained cell under the conditions suitable for the expression of the introduced gene, and analyzing any change caused thereby in the fatty acid composition of the host cell or in the cultured liquid by an ordinary technique. Alternatively, the KAS activity can be confirmed by introducing a DNA produced by linking a gene encoding the protein to the downstream of a promoter which functions in a host cell, into a host cell, culturing the thus-obtained cell under the conditions suitable for the expression of the introduced gene, and subjecting a disruption liquid of the cell to a chain length elongation reaction which uses acyl-ACPs, as substrates.

KAS is categorized into KAS I, KAS II, KAS III and KAS IV according to their substrate specificity. KAS III uses an acetyl-CoA having 2 carbon atoms as the substrate to catalyze the elongation reaction that the number of carbon atoms is increased from 2 to 4. KAS I mainly catalyzes the elongation reaction that the number of carbon atoms is increased from 4 to 16, to synthesize the palmitoyl-ACP having 16 carbon atoms. KAS II mainly catalyzes the elongation reaction to the long-chain acyl group having 18 carbon atoms or more, to synthesize a long-chain acyl-ACP. KAS IV mainly catalyzes the elongation reaction that the acyl-ACP having 6 carbon atoms is converted to the acyl-ACP having 14 carbon atoms, to synthesize a medium-chain acyl-ACP.

As shown in Examples mentioned later, the productivity of long-chain fatty acids having 20, 22, or 24 carbon atoms is improved in the transformant, wherein the expression of the gene encoding the protein (A) or (C) is enhanced. Therefore, the protein (A) to (D) is considered to be a KAS of the type II KAS, having the synthetic activity of long-chain β-ketoacyl-ACP which contains 20 or more carbon atoms. In addition, in the present specification, the term "long-chain β-ketoacyl-ACP synthetic activity" means catalytic activity of an elongation reaction of synthesis of a long-chain β-ketoacyl-ACP having 20 or more carbon atoms by applying an acyl-ACP having mainly 16 or more carbon atoms as a substrate. Moreover, in the present specification, the term "long-chain" means that the number of carbon atoms of the acyl group is 20 or more, and preferably 20, 22, or 24.

Further, according to localization prediction based on ChloroP (http://www.cbs.dtu.dk/services/ChloroP/) or targetP (http://www.cbs.dtu.dk/services/TargetP/), the above-described protein (A) is considered to be a KAS of a chloroplast-localized type and an N-terminal 40 amino acid residue is considered to be a chloroplast transit signal sequence.

The synthetic activity of the KAS to the long-chain β-ketoacyl-ACP can be confirmed by, for example, introducing a DNA produced by linking a gene encoding the protein to the downstream of a promoter which functions in a host cell, into a host cell which lacks a fatty acid degradation system, culturing the thus-obtained cell under the conditions suitable for the expression of the introduced gene, and analyzing any change caused thereby in the fatty acid composition of the host cell or the cultured liquid by an ordinary technique. Alternatively, the synthetic activity to the long-chain β-ketoacyl-ACP can be confirmed by introducing a DNA produced by linking a gene encoding the protein to the downstream of a promoter which functions in a host cell, into a host cell, culturing the thus-obtained cell under the conditions suitable for the expression of the introduced gene, and subjecting a disruption liquid of the cell to a chain length elongation reaction.

The protein (B) consists of an amino acid sequence having 60% or more identity with the amino acid sequence of the protein (A), and has KAS activity. The protein (D) consists of an amino acid sequence having 60% or more identity with the amino acid sequence of the protein (C), and has KAS activity.

In general, it is known that an amino acid sequence encoding an enzyme protein does not necessarily exhibit enzyme activity unless the sequence in the whole region is conserved, and there exists a region in which the enzyme activity is not influenced even if the amino acid sequence is changed. In such a region which is not essential to the enzyme activity, even if the mutation of the amino acid, such as deletion, substitution, insertion and addition thereof is introduced thereinto, the activity inherent to the enzyme can be maintained. Also in the present invention, such a protein can be used in which the KAS activity is kept and a part of the amino acid sequence is subjected to mutation.

In the protein (B), the identity with the amino acid sequence of the protein (A) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of KAS activity. Further, specific examples of the protein (B) include a protein in which 1 or several (for example 1 or more and 190 or less, preferably 1 or more and 166 or less, more preferably 1 or more and 142 or less, further preferably 1 or more and 118 or less, furthermore preferably 1 or more and 95 or less, furthermore preferably 1 or more and 71 or less, furthermore preferably 1 or more and 47 or less, furthermore preferably 1 or more and 38 or less, furthermore preferably 1 or more and 23 or less, furthermore preferably 1 or more and 9 or less, and furthermore preferably 1 or more and 4 or less) amino acids are deleted, substituted, inserted or added to the amino acid sequence of the protein (A).

Further, as the protein (B), it is preferable that the protein consists of an amino acid sequence in which the identity with the amino acid sequence of the protein (A) is 60% or more, the protein has the KAS activity, and from which the chloroplast transit signal sequence is deleted. As described in Examples as mentioned later, productivity of the long-chain fatty acids is further improved by deleting the chloroplast transit signal sequence on a side of an N-terminus in the protein consisting of the amino acid sequence set forth in SEQ ID NO: 1. Such a protein (B) may be a protein consisting of: an amino acid sequence from which an amino acid on the side of the N-terminus is deleted in an arbitrary position of the $1^{st}$ to the $40^{th}$ amino acids of the amino acid sequence set forth in SEQ ID NO: 1 as the amino acid sequence on the side of the N-terminus; and an amino acid sequence of the $41^{st}$ to $475^{th}$ amino acids of the amino acid sequence set forth in SEQ ID NO: 1 as the amino acid sequence on a side of a C-terminus.

Moreover, the protein (B) also preferably includes a protein consisting of an amino acid sequence formed such that a signal peptide engaging in transport or secretion of the protein is added to the amino acid sequence of the protein (A) or (B).

The protein (C) consists of an amino acid sequence of the $41^{st}$ to 475th amino acids of the amino acid sequence set forth in SEQ ID NO: 1 and a methionine residue added on the side of the N-terminus. Note that the protein (B) also includes the protein (C). In the protein (C), from the protein consisting of the amino acid sequence set forth in SEQ ID NO: 1, the chloroplast transit signal sequence (the $1^{st}$ to $40^{th}$ amino acid residues of the amino acid sequence set forth in SEQ ID NO: 1) on the side of the N-terminus is deleted.

In the protein (D), the identity with the amino acid sequence of the protein (C) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of KAS activity. Further, specific examples of the protein (D) include a protein in which 1 or several (for example 1 or more and 174 or less, preferably 1 or more and 152 or less, more preferably 1 or more and 130 or less, further preferably 1 or more and 108 or less, furthermore preferably 1 or more and 87 or less, furthermore preferably 1 or more and 65 or less, furthermore preferably 1 or more and 43 or less, furthermore preferably 1 or more and 34 or less, furthermore preferably 1 or more and 21 or less, furthermore preferably 1 or more and 8 or less, and furthermore preferably 1 or more and 4 or less) amino acids are deleted, substituted, inserted or added to the amino acid sequence of the protein (C).

Moreover, the protein (D) also preferably includes a protein consisting of an amino acid sequence formed such that a signal peptide engaging in transport or secretion of the protein is added to the amino acid sequence of the protein (C) or (D).

A method of introducing the mutation into an amino acid sequence includes a method of, for example, introducing a mutation into a nucleotide sequence encoding the amino acid sequence. A method of introducing the mutation includes a method of introducing a site-specific mutation. Specific examples of the method of introducing the site-specific mutation include a method of utilizing the SQE-PCR reaction, the ODA method, and the Kunkel method.

Further, commercially available kits such as Site-Directed Mutagenesis System Mutan-Super Express Km kit (Takara Bio), Transformer™ Site-Directed Mutagenesis kit (Clontech Laboratories), and KOD-Plus-Mutagenesis Kit (TOYOBO) can also be utilized. Furthermore, a gene containing a desired mutation can also be obtained by introducing a genetic mutation at random, and then performing an evaluation of the enzyme activities and a gene analysis thereof by an appropriate method.

The proteins (A) to (D) can be obtained by chemical techniques, genetic engineering techniques or the like that are ordinarily carried out. For example, a natural product-derived protein can be obtained through isolation, purification and the like from *Nannochloropsis oculata*. In addition, the proteins (A) to (D) can be obtained by artificial chemical synthesis based on the amino acid sequence set forth in SEQ ID NO: 1. Alternatively, as recombinant proteins, proteins (A) to (D) may also be produced by gene recombination technologies. In the case of producing a recombinant protein, the β-ketoacyl-ACP synthase gene described below can be used.

Note that the algae such as *Nannochloropsis oculata* can be obtained from culture collection such as private or public research institutes or the like. For example, *Nannochloropsis oculata* NIES-2145 can be obtained from National Institute for Environmental Studies (NIES).

An example of the gene encoding the protein (A) to (D) (hereinafter, also referred to as "KAS gene") includes a gene consisting of at least any one of the following DNAs (a) to (d) (hereinafter, also referred to as "NoKASII gene").

(a) a DNA consisting of the nucleotide sequence set forth in SEQ ID NO: 2;
(b) a DNA consisting of a nucleotide sequence having 60% or more identity with the nucleotide sequence of the DNA (a), and encoding the protein having KAS activity;
(c) a DNA consisting of the nucleotide sequence set forth in SEQ ID NO: 45; and
(d) a DNA consisting of a nucleotide sequence having 60% or more identity with the nucleotide sequence of the DNA (c), and encoding the protein having KAS activity.

The nucleotide sequence set forth in SEQ ID NO: 2 is a nucleotide sequence of a gene encoding a protein (KAS derived from *Nannochloropsis oculata* NIES-2145) consisting of the amino acid sequence set forth in SEQ ID NO: 1.

In the DNA (b), the identity with the nucleotide sequence of the DNA (a) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of KAS activity. Further, the DNA (b) is also preferably a DNA in which 1 or several (for example 1 or more and 571 or less, preferably 1 or more and 499 or less, more preferably 1 or more and 428 or less, further preferably 1 or more and 357 or less, further preferably 1 or more and 285 or less, further preferably 1 or more and 214 or less, further preferably 1 or more and 142 or less, further preferably 1 or more and 114 or less, further preferably 1 or more and 71 or less, further preferably 1 or more and 28 or less, and furthermore preferably 1 or more and 14 or less) nucleotides are deleted, substituted, inserted or added to the nucleotide sequence set forth in SEQ ID NO: 2, and encoding a protein (A) or (B) having KAS activity. Furthermore, the DNA (b) is also preferably a DNA capable of hybridizing with a DNA consisting of the nucleotide sequence complementary with the DNA (a) under a stringent condition, and encoding the protein (A) or (B) having KAS activity.

Further, as the DNA (b), it is preferable that the DNA consists of a nucleotide sequence in which the identity with the nucleotide sequence of the DNA (a) is 60% or more, and encodes the protein (A) or (B) having KAS activity, and from which the nucleotide sequence encoding the chloroplast transit signal sequence is deleted. As described in Examples as mentioned later, productivity of the long-chain fatty acids is further improved by deleting the chloroplast transit signal sequence on a side of an N-terminus in the protein consisting of the amino acid sequence set forth in SEQ ID NO: 1. The DNA encoding such the protein may be a DNA consisting of: a nucleotide sequence from which a nucleotide on the side of the 5' end is deleted in an arbitrary position of the $1^{st}$ to the $120^{th}$ nucleotides of the nucleotide sequence set forth in SEQ ID NO: 2 as the nucleotide sequence on the side of the 5' end; and a nucleotide sequence of the $121^{st}$ to $1428^{th}$ nucleotides of the nucleotide sequence set forth in SEQ ID NO: 2 as the nucleotide sequence on a side of a 3' end.

Moreover, the DNA (b) also preferably includes a DNA consisting of a nucleotide sequence encoding such that a signal peptide engaging in transport or secretion of the protein is added to the nucleotide sequence of the DNA (a) or (b).

The DNA (c) consists of a nucleotide sequence of the $121^{st}$ to $1428^{th}$ nucleotides of the nucleotide sequence set forth in SEQ ID NO: 2 and a start codon (ATG) added on the side of the 5' end, and encoding the protein (C) (a protein consisting of the amino acid sequence set forth in SEQ ID 44). Note that the above-described DNA (b) also includes the DNA (c). In the DNA (c), from the DNA consisting of the nucleotide sequence set forth in SEQ ID NO: 2, the nucleotide sequence encoding the chloroplast transit signal sequence (the $1^{st}$ to $120^{th}$ nucleotides of the nucleotide sequence set forth in SEQ ID NO: 2) is deleted.

In the DNA (d), the identity with the nucleotide sequence of the DNA (c) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of KAS activity. Further, the DNA (d) is also preferably a DNA in which 1 or several (for example 1 or more and 523 or less, preferably 1 or more and 457 or less, more preferably 1 or more and 392 or less, further preferably 1 or more and 327 or less, further preferably 1 or more and 261 or less, further preferably 1 or more and 196 or less, further preferably 1 or more and 130 or less, further preferably 1 or more and 104 or less, further preferably 1 or more and 65 or less, further preferably 1 or more and 26 or less, and furthermore preferably 1 or more and 13 or less) nucleotides are deleted, substituted, inserted or added to the nucleotide sequence of the DNA (c), and encoding a protein (C) or (D) having KAS activity. Furthermore, the DNA (d) is also preferably a DNA capable of hybridizing with a DNA consisting of the nucleotide sequence complementary with the DNA (c) under a stringent condition, and encoding the protein (C) or (D) having KAS activity.

Moreover, the DNA (d) also preferably includes a DNA consisting of a nucleotide sequence encoding such that a signal peptide engaging in transport or secretion of the protein is added to the nucleotide sequence of the DNA (c) or (d).

A method of promoting the expression of the KAS gene can be appropriately selected from an ordinarily method. For example, a method of introducing the KAS gene into cyanobacteria, and a method of modifying expression regulation regions of the gene (promoter, terminator, or the like) in cyanobacteria having the KAS gene on a genome, can be selected. Especially, the method of introducing the KAS gene into cyanobacteria to enhancing the KAS gene expression is preferable.

Hereinafter, in the present specification, a cell in which expression of a gene encoding a target protein herein is enhanced is also referred to as the "transformant", and a cell in which the expression of the gene encoding the target protein is not enhanced is also referred to as the "host" or "wild type strain".

In the transformant used in the present invention, the ability to produce long-chain fatty acids and lipids containing these long-chain fatty acids as components (a production amount of long-chain fatty acids and lipids containing these long-chain fatty acids as components, or a proportion of long-chain fatty acids and lipids containing these long-chain fatty acids as components in the total fatty acids or lipids to be produced) is tend to increase, in comparison with a host. Moreover, as a result, in the transformant, the fatty acid composition in the lipid is modified. Therefore, the present invention using the transformant can be preferably applied to production of lipids having specific number of carbon atoms, particularly long-chain fatty acids and lipids containing these long-chain fatty acids as components, preferably fatty acids having 20 or more carbon atoms and lipids containing these fatty acids as components, more preferably fatty acids having 20 to 24 carbon atoms and lipids containing these fatty acids as components, further preferably fatty acids having 20, 22 or 24 carbon atoms and lipids containing these fatty acids as components, further preferably saturated fatty acids having 20, 22 or 24 carbon atoms, mono-unsaturated fatty acids, or di-unsaturated fatty acids, and lipids containing these fatty acids as components, and still further preferably saturated fatty acids having 20, 22 or 24 carbon atoms or mono-unsaturated fatty acids, and lipids containing these fatty acids as components.

The ability to produce fatty acids and lipids of the host and the transformant can be measured by the method used in Examples described below.

The method of introducing the KAS gene into cyanobacteria and enhancing the expression of the gene is described.

The KAS gene can be obtained by genetic engineering techniques that are ordinarily carried out. For example, the KAS gene can be artificially synthesized based on the amino acid sequence set forth in SEQ ID NO: 1 or the nucleotide sequence set forth in SEQ ID NO: 2. The synthesis of the KAS gene can be achieved by utilizing, for example, the services of Invitrogen. Further, the gene can also be obtained by cloning from *Nannochloropsis oculata*. The cloning can be carried out by, for example, the methods described in Molecular Cloning: A LABORATORY MANUAL THIRD EDITION [Joseph Sambrook, David W. Russell, Cold Spring Harbor Laboratory Press (2001)]. Furthermore, *Nannochloropsis oculata* NIES-2145 used in Examples can be obtained from National Institute for Environmental Studies (NIES).

The transformant that can be preferably used in the present invention is obtained by introducing the KAS gene into cyanobacteria according to an ordinarily method. Specifically, the transformant can be produced by preparing a recombinant vector or a gene expression cassette which is capable of expressing the KAS gene in a cyanobacteria cell, introducing this vector or cassette into a cyanobacteria cell, and thereby transforming the host cell.

Cyanobacteria used as the host of the transformant of the present invention are one group of prokaryotes that perform photosynthesis using chlorophyll.

Cyanobacteria are highly diversified. In view of cell morphology, there are bacteria having a unicellular shape such as *Synechocystis* sp. PCC6803, bacteria having a filamentous shape formed of many cells connected like a string such as *Anabaena* sp. PCC7120 forming heterocysts and fixing nitrogen, bacteria having a spiral shape and a branched shape, and the like.

In view of growth environment, there are species adapted in various conditions including thermophilic bacteria such as *Thermosynechococcus elongatus* BP-1 isolated from Beppu Onsen; and oceanic bacteria such as *Synechococcus* sp. CC9311 living in the coast or *Synechococcus* sp. WH8102 living in the outer sea.

As bacteria having feature intrinsic to the species, *Microcystis aeruqinosa*, which has gas vacuoles and can produce toxin; *Gloeobacter violaceus* PCC7421 having no thylakoid and a light harvesting antenna, i.e., phycobilisome, bound to plasma membrane; and oceanic *Acaryochloris marina* having chlorophyll d as a main (>95%) photosynthetic pigment in place of chlorophyll a, as is in general photosynthetic organisms, are also mentioned.

In cyanobacteria, carbon dioxide fixed by photosynthesis is converted into acetyl-CoA via a large number of enzymatic reaction processes. In the initial stage of fatty acid synthesis, malonyl-CoA is synthesized from acetyl-CoA and $CO_2$ by the function of acetyl-CoA carboxylase. Next, malonyl-CoA is converted into malonyl-ACP by the function of malonyl-CoA:ACP transacylase. Thereafter, while β-ketoacyl-acyl-ACP synthetase progressively works, two carbon units are sequentially added to synthesize acyl-ACP, which are increased in two carbons and used as an intermediate for synthesizing e.g., a membrane lipid.

Every kind of cyanobacteria can be used as the host of the transformant of the present invention. Specific examples of the cyanobacteria include cyanobacteria of the genus *Synechocystis*, the genus *Synechococcus*, the genus *Thermosynechococcus*, the genus *Trichodesmium*, the genus *Acaryochloris*, the genus *Crocosphaera*, and the genus *Anabaena*. Among these, cyanobacteria of the genus *Synechocystis*, the genus *Synechococcus*, the genus *Thermosynechococcus*, or the genus *Anabaena* are preferable, and cyanobacteria of the genus *Synechocystis* or the genus *Synechococcus* are more preferable. Further, the host used in the present invention is preferably *Synechocystis* sp. PCC6803, *Synechocystis* sp. PCC7509, *Synechocystis* sp. PCC6714, *Synechococcus elongatus* sp. PCC7942, *Thermosynechococcus elongatus* BP-1, *Trichodesmium erythraeum* IMS101, *Acaryochloris mariana* MBIC11017, *Crocosphaera watsonii* WH8501, or *Anabaena* sp. PCC7120, more preferably *Synechocystis* sp. PCC6803 or *Synechococcus elongatus* sp. PCC7942.

A vector for use as the plasmid vector for gene expression or a vector containing the gene expression cassette (plasmid) may be any vector capable of introducing the gene encoding the objective protein into a host, and expressing the gene in the host cell. For example, a vector which has expression regulation regions such as a promoter and a terminator in accordance with the type of the host to be introduced, and has a replication initiation point, a selection marker or the like, can be used. Furthermore, the vector may also be a vector such as a plasmid capable of self-proliferation and self-replication outside the chromosome, or may also be a vector which is incorporated into the chromosome.

Specific examples of the expression vector that can be preferably used in the present invention include a pUC-based vector (manufactured by Takara Bio), pBluescript (pBS) II SK(−) (manufactured by Stratagene), a pSTV-based vector (manufactured by Takara Bio), a pET-based vector (manufactured by Takara Bio), a pGEX-based vector (manufactured by GE Healthcare), a pCold-based vector (manufactured by Takara Bio), pHY300PLK (manufactured by Takara Bio), pUB110 (Plasmid, 1986, vol. 15(2), p. 93-103), pBR322 (manufactured by Takara Bio), pRS403 (manufactured by Stratagene), pMW218/219 (manufactured by Nippon Gene), a pRI-based vector (manufactured by Takara Bio), a pBI-based vector (manufactured by Clontech), and an IN3-based vector (manufactured by Inpianta Innovations). Among these, a pUC-based vector is more preferable.

Moreover, a kind of promoter regulating the expression of the gene encoding an objective protein introduced into the expression vector can also be appropriately selected according to a kind of the host to be used. Specific examples of the promoter that can be preferably used in the present invention include lac promoter, trp promoter, tac promoter, trc promoter, T7 promoter, SpoVG promoter, a promoter that relates to a derivative that can be derived by addition of isopropyl β-D-1-thiogalactopyranoside (IPTG), Rubisco operon (rbc), PSI reaction center protein (psaAB), D1 protein of PSII (psbA), c-phycocyanin β subunit (cpcB), and a promoter of a rrnA operon gene encoding ribosomal RNA. Among these, trc promoter or cpc promoter is more preferable.

Moreover, a kind of selection marker for confirming introduction of the objective DNA fragments can also be appropriately selected according to a kind of the host to be used. Examples of the selection marker that can be preferably used in the present invention include drug resistance genes such as a chloramphenicol resistance gene, an erythromycin resistance gene, a neomycin resistance gene, a kanamycin resistance gene, a spectinomycin resistance gene, and a gentamicin resistance gene. Further, it is also possible to use a deletion of an auxotrophy-related gene or the like as the selection marker gene.

Introduction of the gene encoding an objective protein to the vector can be conducted by an ordinary technique such as restriction enzyme treatment and ligation.

Further, the heterogeneous gene to be introduced into cyanobacteria is preferably optimized in codon in accordance with use frequency of codon in the cyanobacteria. Information of codons used in each of organisms is available from Codon Usage Database (www.kazusa.or.jp/codon/).

Furthermore, the method for transformation can be appropriately selected from ordinary techniques according to a kind of the host to be used. Specific examples of the method for transformation include a spontaneous transformation method, an electroporation method, and a jointing method.

The KAS gene introduced into the cyanobacteria is preferably incorporated on the genome of cyanobacteria by homologous recombination or the like. A position into which the KAS gene is incorporated on the genome can be appropriately set. For example, the KAS gene is preferably incorporated into a neutral site such as a slr0168 region or an NS1 region on the genome of cyanobacteria.

The transformant of the present invention has the ability to produce the long-chain fatty acids or the lipids containing these long-chain fatty acids as the components, in which the cyanobacteria originally don't possess such the ability. Then, the productivity is improved in comparison with a host in which expression of the gene encoding at least any one of the proteins (A) to (D) is not enhanced. Accordingly, if the transformant of the present invention is cultured under suitable conditions and then the long-chain fatty acids or the lipids containing these fatty acids as components are collected from an obtained cultured product or an obtained growth product, the long-chain fatty acids or the lipids containing these fatty acids as components can be efficiently produced. Herein, the "cultured product" means medium and a transformant subjected to cultivation, and the "growth product" means a transformant subjected to growth.

The transformant of the present invention can be cultured, according to liquid culture or a modified method thereof, by using a medium to be ordinarily used for culture of cyanobacteria, such as a BG-11 medium (J. Gen. Microbial., 1979, vol. 111, p. 1-61), an A medium (Proc. Natl. Acad. Sci. U.S.A., 1980, vol. 77, p. 6052-6056) and an AA medium (Plant Physiol., 1955, vol. 30, p. 366-372).

The culture for producing lipid may be performed in a period during which bacterial cells are sufficiently grown to accumulate fatty acids in high concentrations, for example, from 7 to 45 days, preferably from 7 to 30 days, and more preferably from 10 to 14 days, by an aeration/spinner culture or shaking culture.

The method of collecting lipid produced in the cultured product or growth product can be appropriately selected from ordinary techniques. For example, lipid components can be isolated and collected from the above-described cultured product or growth product by means of filtration, centrifugation, cell disruption, gel filtration chromatography, ion exchange chromatography, chloroform/methanol extraction, hexane extraction, or ethanol extraction. In the case of cultivation of larger scales, lipid can be obtained by collecting oil components from the cultured product or growth product through pressing or extraction, and then performing general purification processes such as degumming, deacidification, decoloration, dewaxing, and deodorization. After lipid components are isolated as such, the isolated lipid is hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

The lipids produced in the production method of the present invention are formed by containing a polar lipid being one kind of glycerol ester of fatty acids. Specific examples of the polar lipid include monogalactosyldiacylglycerol (MGDG), digalactosyldiacylglycerol (DGDG), sulfoquinovosyldiacylglycerol (SQDG), and phosphatidylglycerol (PG).

In view of usability for an industrial raw material for a dispersing agent, the fatty acid or the ester compound thereof contained in the lipid is preferably a long-chain fatty acid or a fatty acid ester compound thereof, more preferably a fatty acid having 20 or more carbon atoms or a fatty acid ester compound thereof, more preferably a fatty acid having 20 to 24 carbon atoms or a fatty acid ester compound thereof, more preferably a fatty acid having 20, 22, or 24 carbon atoms or a fatty acid ester compound thereof, more preferably a saturated fatty acid having 20, 22, or 24 carbon atoms, a mono-unsaturated fatty acid, or a di-unsaturated fatty acid, or a fatty acid ester compound thereof, and furthermore preferably a saturated fatty acid having 20, 22, or 24 carbon atoms or a mono-unsaturated fatty acid, or a fatty acid ester thereof.

The lipid obtained by the present invention can be utilized for food, as well as a plasticizer, an emulsifier incorporated into cosmetic products or the like, a cleansing agent such as a soap or a detergent, a fiber treatment agent, a hair conditioning agent, a disinfectant or an antiseptic.

With regard to the embodiments described above, the present invention also discloses methods of producing lipids, methods of improving productivity of lipids, methods of modifying composition of fatty acids to be produced, transformants, and methods of preparing transformants, described below.

<1> A method of producing lipids, containing the steps of:
culturing a transformant in which the expression of a gene encoding at least any one of the following proteins (A) to (D) is enhanced in a cyanobacteria cell, and
producing fatty acids or the lipids containing these fatty acids as components.
(A) a protein consisting of the amino acid sequence set forth in SEQ ID NO: 1;
(B) a protein consisting of an amino acid sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more identity with the amino acid sequence of the protein (A), and having KAS activity;
(C) a protein consisting of the amino acid sequence set forth in SEQ ID NO: 44; and
(D) a protein consisting of an amino acid sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more identity with the amino acid sequence of the protein (C), and having KAS activity.

<2> A method of improving lipid productivity, containing the steps of:
enhancing the expression of a gene encoding at least any one of the proteins (A) to (D) in a cyanobacteria cell, and
improving the productivity of long-chain fatty acids or the lipids containing these fatty acids as components, produced in a cyanobacteria cell.

<3> A method of modifying the composition of lipids, containing the steps of:
enhancing the gene expression of a gene encoding at least any one of the proteins (A) to (D) in a cyanobacteria cell, and
modifying the composition of fatty acids or lipids containing these fatty acids as components produced in a cyanobacteria cell.

<4> The method dscribed in the above item <3>, wherein the proportion of long-chain fatty acids in the total of fatty acids to be produced increases.

<5> A method of providing an ability to produce long-chain fatty acids or lipids containing these fatty acids as components with cyanobacteria, containing the step of enhancing the expression of a gene encoding at least any one of the proteins (A) to (D) in a cyanobacteria cell.

<6> The method described in any one of the above items <1> to <5>, wherein a gene encoding at least any one of the proteins (A) to (D) is introduced into cyanobacteria, preferably into a neutral site on genome of cyanobacteria, to enhance the above-described gene.

<7> The method described in any one of the above items <1> to <6>, wherein the protein (B) consists of an amino acid sequence in which 1 or several amino acids, preferably 1 or more and 190 or less amino acids, more preferably 1 or more and 166 or less amino acids, further preferably 1 or more and 142 or less amino acids, furthermore preferably 1 or more and 118 or less amino acids, furthermore preferably 1 or more and 95 or less amino acids, furthermore preferably 1 or more and 71 or less amino acids, furthermore preferably 1 or more and 47 or less amino acids, furthermore preferably 1 or more and 38 or less amino acids, furthermore preferably 1 or more and 23 or less amino acids, furthermore preferably 1 or more and 9 or less amino acids, and furthermore preferably 1 or more and 4 or less amino acids, are deleted, substituted, inserted or added to the amino acid sequence of the protein (A).

<8> The method described in any one of the above items <1> to <6>, wherein the protein (D) consists of an amino acid sequence in which 1 or several amino acids, preferably 1 or more and 174 or less amino acids, more preferably 1 or more and 152 or less amino acids, further preferably 1 or more and 130 or less amino acids, furthermore preferably 1 or more and 108 or less amino acids, furthermore preferably 1 or more and 87 or less amino acids, furthermore preferably 1 or more and 65 or less amino acids, furthermore preferably 1 or more and 43 or less amino acids, furthermore preferably 1 or more and 34 or less amino acids, furthermore preferably 1 or more and 21 or less amino acids, furthermore preferably 1 or more and 8 or less amino acids, and furthermore preferably 1 or more and 4 or less amino acids, are deleted, substituted, inserted or added to the amino acid sequence of the protein (C).

<9> The method described in any one of the above items <1> to <8>, wherein the proteins (A) to (D) are KASs having the synthetic activity of long-chain 3-ketoacyl-ACP.

<10> The method described in any one of the above items <1> to <9>, wherein the gene encoding at least any one of the proteins (A) to (D) is a gene consisting of any one of the following DNAs (a) to (d):
(a) a DNA consisting of the nucleotide sequence set forth in SEQ ID NO: 2;
(b) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more, identity with the nucleotide sequence of the DNA (a) and encoding a protein having KAS activity;
(c) a DNA consisting of the nucleotide sequence set forth in SEQ ID NO: 45; and
(d) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more, identity with the nucleotide sequence of the DNA (c) and encoding a protein having KAS activity.

<11> The method described in the above item <10>, wherein the DNA (b) is a DNA consisting of a nucleotide sequence in which 1 or several nucleotides, preferably 1 or more and 571 or less nucleotides, more preferably 1 or more and 499 or less nucleotides, further preferably 1 or more and 428 or less nucleotides, furthermore preferably 1 or more and 357 or less nucleotides, furthermore preferably 1 or more and 285 or less nucleotides, furthermore preferably 1 or more and 214 or less nucleotides, furthermore preferably 1 or more and 142 or less nucleotides, furthermore preferably 1 or more and 114 or less nucleotides, furthermore preferably 1 or more and 71 or less nucleotides, furthermore preferably 1 or more and 28 or less nucleotides, and furthermore preferably 1 or more and 14 or less nucleotides, are deleted, substituted, inserted or added to the nucleotide sequence of the DNA (a), and encoding the protein (A) or (B) having KAS activity, or a DNA capable of hybridizing with a DNA consisting of a nucleotide sequence complementary with the DNA (a) under a stringent condition, and encoding the protein (A) or (B) having KAS activity.

<12> The method described in the above item <10>, wherein the DNA (d) is a DNA consisting of a nucleotide sequence in which 1 or several nucleotides, preferably 1 or more and 523 or less nucleotides, more preferably 1 or more and 457 or less nucleotides, further preferably 1 or more and 392 or less nucleotides, furthermore preferably 1 or more and 327 or less nucleotides, furthermore preferably 1 or more and 261 or less nucleotides, furthermore preferably 1 or more and 196 or less nucleotides, furthermore preferably 1 or more and 130 or less nucleotides, furthermore preferably 1 or more and 104 or less nucleotides, furthermore preferably 1 or more and 65 or less nucleotides, furthermore preferably 1 or more and 26 or less nucleotides, and furthermore preferably 1 or more and 13 or less nucleotides, are deleted, substituted, inserted or added to the nucleotide sequence of the DNA (c), and encoding the protein (C) or (D) having KAS activity, or a DNA capable of hybridizing with a DNA consisting of a nucleotide sequence complementary with the DNA (c) under a stringent condition, and encoding the protein (C) or (0) having KAS activity.

<13> The method described in any one of the above items <1> to <12>, wherein the cyanobacteria are cyanobacteria selected from the group consisting of the genus *Synechocystis*, the genus *Synechococcus*, the genus *Thermosynechococcus*, the genus *Trichodesmium*, the genus *Acaryochloris*, the genus *Crocosphaera*, and the genus *Anabaena*, preferably cyanobacteria of the genus *Synechocystis* or the genus *Synechococcus*.

<14> The method described in any one of the above items <1> to <13>, wherein the lipid contains a long-chain fatty acid or a fatty acid ester compound thereof, preferably a fatty acid having 20 or more carbon atoms or a fatty acid ester compound thereof, more preferably a fatty acid having 20 to 24 carbon atoms or a fatty acid ester compound thereof, more preferably a fatty acid having 20, 22, or 24 carbon atoms or a fatty acid ester compound thereof, more preferably a saturated fatty acid having 20, 22, or 24 carbon atoms, a mono-unsaturated fatty acid, or a di-unsaturated fatty acid, or a fatty acid ester compound thereof, and furthermore preferably a saturated fatty acid having 20, 22, or 24 carbon atoms or a mono-unsaturated fatty acid, or a fatty acid ester compound thereof.

<15> The method described in any one of the above items <1> to <14>, culturing the cyanobacteria using BG-11 medium.

<16> A transformant, wherein the expression of a gene encoding at least any one of the proteins (A) to (D) is enhanced in a cyanobacteria cell.

<17> A transformant, wherein a gene encoding at least any one of the proteins (A) to (D), or a recombinant vector containing thereof is introduced into cyanobacteria.

<18> A method of producing a transformant, containing introducing the gene encoding at least any one of the proteins (A) to (D), or a recombinant vector containing thereof into cyanobacteria.

<19> The transformant or the method of producing the same described in any one of the above items <16> to <17>, wherein the protein (A) to (D) is a protein specified in the above item <6> or <7>, respectively.

<20> The transformant or the method of producing the same described in any one of the above items <16> to <19>, wherein a gene encoding at least any one of the proteins (A) to (D) is a gene consisting of any one of the DNAs (a) to (d).
<21> The transformant or the method of producing the same described in the above item <20>, wherein the DNA (b) or (d) is a DNA specified in the above item <11> or <12>, respectively.
<22> The transformant or the method of producing the same described in any one of the above items <16> to <21>, wherein the cyanobacteria are cyanobacteria selected from the group consisting of the genus *Synechocystis*, the genus *Synechococcus*, the genus *Thermosynechococcus*, the genus *Trichodesmium*, the genus *Acaryochloris*, the genus *Crocosphaera*, and the genus *Anabaena*, preferably cyanobacteria of the genus *Synechocystis* or the genus *Synechococcus*.
<23> Use of the transformant or a transformant obtained by the method of producing a transformant described in any of the above items <16> to <22>, for producing a lipid.
<24> The use described in the above item <23>, wherein the lipid contains a long-chain fatty acid or a fatty acid ester compound thereof, preferably a fatty acid having 20 or more carbon atoms or a fatty acid ester compound thereof, more preferably a fatty acid having 20 to 24 carbon atoms or a fatty acid ester compound thereof, more preferably a fatty acid having 20, 22, or 24 carbon atoms or a fatty acid ester compound thereof, more preferably a saturated fatty acid having 20, 22, or 24 carbon atoms, a mono-unsaturated fatty acid, or a di-unsaturated fatty acid, or a fatty acid ester compound thereof, and furthermore preferably a saturated fatty acid having 20, 22, or 24 carbon atoms or a mono-unsaturated fatty acid, or a fatty acid ester compound thereof.

EXAMPLES

Hereinafter, the present invention will be described more in detail with reference to Examples, but the present invention is not limited thereto. Herein, the nucleotide sequences of the primers used in Examples are shown in Tables 1 and 2.

TABLE 1

| Primer | Nucleotide sequence | SEQ ID NO: |
|---|---|---|
| pUC118/slr0168up-F | 5'-GGATCCTCTAGAGTCATCGCCTGTTGGCCTACC-3' | 3 |
| Kmr/slr0168up-R | 5'-TTCGCTGGGTTTATCTACCGTTCAAATTCTGTGGG-3' | 4 |
| Kmr/slr0168down-F | 5'-GGAATTTGTATCGATAGCGGAAGATATTACGGGAC-3' | 6 |
| pUC118/slr0168down-R | 5'-GCATGCCTGCAGGTCAATCACGTTGGGTCCCAAG-3' | 7 |
| Kmr-F | 5'-GATAAACCCAGCGAACCA-3' | 9 |
| Kmr-R | 5'-ATCGATACAAATTCCTCG-3' | 10 |
| slr0168up-R | 5'-TACCGTTCAAATTCTGTGGG-3' | 12 |
| slr0168up/Pcpc560-F | 5'-AGAATTTGAACGGTAACCTGTAGAGAAGAGTCCCTG-3' | 13 |
| Pcpc560-R | 5'-TGAATTAATCTCCTACTTGAC-3' | 14 |
| Trbc-F | 5'-GTTACAGTTTTGGCAATTAC-3' | 16 |
| Km/Trbc-R | 5'-TTCGCTGGGTTTATCTTCCCCACTTAGATAAAAAATCC-3' | 17 |
| Pcpc560/NoKASII-F | 5'-TAGGAGATTAATTCAATGATGGAGAAGCTGACCCTC-3' | 19 |
| Trbc/NoKASII-R | 5'-TGCCAAAACTGTAACCTAGGCAACATACTTCTTGAAGACC-3' | 20 |
| Pcpc560/NoKASII(-40)-F | 5'-TAGGAGATTAATTCAATGACTGTGCGTCGTGCATCAG-3' | 21 |
| Pcpc560/AtKASII-F | 5'-TAGGAGATTAATTCAATGGTGGGTGCGTCTTCCTC-3' | 22 |
| Trbc/AtKASII-R | 5'-TGCCAAAACTGTAACTCACTTGTAAGGAGCAAAAATGATGC-3' | 23 |

TABLE 2

| Primer | Nucleotide sequence | SEQ ID NO: |
|---|---|---|
| pUC118/NS1up-F | 5'-GGATCCTCTAGAGTCAATGCCTTCTCCAAGGGCGGC-3' | 25 |
| Kmr/NS1up-R | 5'-TTCGCTGGGTTTATCCTTCTGGAGCAGGAAGATGTCG-3' | 26 |
| Kmr/NS1down-F | 5'-GGAATTTGTATCGATTCGAGTCCCTGCTCGTCACGC-3' | 28 |
| pUC118/NS1down-R | 5'-GCATGCCTGCAGGTCCGGCATGGCAATGTCTCTCTG-3' | 29 |

TABLE 2-continued

| Primer | Nucleotide sequence | SEQ ID NO: |
|---|---|---|
| NS1down-F | 5'-TCGAGTCCCTGCTCGTCACGC-3'-3' | 31 |
| Kmr/Ptrc-F | 5'-GGAATTTGTATCGATTTGACAATTAATCATCCGGCTCG-3' | 32 |
| Ptrc-R | 5'-GGTCTGTTTCCTGTGTGAAATTG-3' | 33 |
| NS1down/Trbc-R | 5'-CGAGCAGGGACTCGATTCCCCACTTAGATAAAAAATCC-3' | 35 |
| Ptrc/NoKASII-F | 5'-CACAGGAAACAGACCATGATGGAGAAGCTGACCCTC-3' | 36 |
| Ptrc/NoKASII(-40)-F | 5'-CACAGGAAACAGACCATGACTGTGCGTCGTGCATCAG-3' | 37 |
| Ptrc/AtKASII-F | 5'-CACAGGAAACAGACCATGGTGGGTGCGTCTTCCTC-3' | 38 |
| Ptrc/EcKASII-F | 5'-CACAGGAAACAGACCATGTCTAAGCGTCGTGTAGTTGTG-3' | 39 |
| Trbc/EcKASII-R | 5'-TGCCAAAACTGTAACTTAGATCTTTTTAAAGATCAAAGAACC-3' | 40 |

Preparation Example 1 Preparation of a Transformant Which is Obtained by Introducing a NoKASII Gene into Cyanobacteria (1) Construction of Plasmid for Kanamycin Resistance Gene Expression Using genome DNA of the wild-type strains of *Synechocystis* sp. strain PCC6803 as a template, and the primer pUC118/slr0168up-F (SEQ ID NO: 3) and the primer Kmr/slr0168up-R (SEQ ID NO: 4) described in Table 1, PCR was carried out to amplify the upstream fragment of a neutral site slr0168 region (slr0168up fragment; SEQ ID NO: 5). Further, using the genome DNA described above, and the primer Kmr/slr0168down-F (SEQ ID NO: 6) and the primer pUC118/slr0168down-R (SEQ ID NO: 7) described in Table 1, PCR was carried out to amplify the downstream fragment of a neutral site slr0168 region (slr0168down fragment; SEQ ID NO: 8).

Furthermore, using a plasmid of pJH1 (Gene, 1983, vol. 23, p. 331-341) as a template, and the primers Kmr-F (SEQ ID NO: 9) and Kmr-R (SEQ ID NO: 10), kanamycin resistance marker gene fragment (Kmr fragment; SEQ ID NO: 11).

A pUC118-slr0168::Km plasmid was obtained by inserting the slr0168up fragment, slr0168down fragment, and Kmr fragment into the HincII site of the pUC118 plasmid (manufactured by Takara Bio) by using the In-Fusion (registered trademark) PCR cloning method (Clontech).

(2) Construction of Plasmid for NoKASII Gene Expression

The pUC118-slr0168::Km plasmid was used as a template, and PCR was carried out by using the primer Kmr-F (SEQ ID NO: 9) and the primer slr0168up-R (SEQ ID NO: 12) described in Table 1 to linearize the pUC118-slr0168::Km plasmid.

Then, PCR was carried out by using genome DNA of the wild-type strains of *Synechocystis* sp. strain PCC6803, and the primer slr0168up/Pcpc560-F (SEQ ID NO: 13) and the primer Pcpc560-R (SEQ ID NO: 14) described in Table 1, to amplify a high expression cpc560 promoter fragment (Scientific Reports, 2014, vol. 4, p. 4500, Pcpc560 fragment; SEQ ID NO: 15).

Further, PCR was carried out by using genome DNA of the wild-type strains of *Synechocystis* sp. strain PCC6803, and the primer Trbc-F (SEQ ID NO: 16) and the primer Km/Trbc-R (SEQ ID NO: 17) described in Table 1 to amplify a terminator region of a rbc gene (Trbc fragment; SEQ ID NO: 18).

Furthermore, using a cDNA library prepared from *Nannochloropsis oculata* strain NIES-2145 as a template, and the primer Pcpc560/NoKASII-F (SEQ ID NO: 19) and the primer Trbc/NoKASII-R (SEQ ID NO: 20) described in Table 1 to amplify a NoKASII fragment (SEQ ID NO: 2).

Then, the linearized pUC118-slr0168::Km plasmid, the Pcpc560 fragment, the Trbc fragment, and the NoKASII fragment were mixed, and the resultant mixture was cloned by using the In-Fusion (registered trademark) PCR Cloning method (Clontech) to obtain pUC118-slr0168::Pcpc560-NoKASII-Trbc-Km plasmid in which the cpc560 promoter, the NoKASII gene, the rbc terminator, and the kanamycin resistance gene cassette were inserted in this order into a neutral site slr0168 region derived from *Synechocystis* sp. strain PCC6803.

(3) Transformation of Cyanobacteria Using the Plasmid for NoKASII Gene Expression Using thus-obtained pUC118-slr0168::Pcpc560-NoKASII-Trbc-Km plasmid, *Synechocystis* sp. strain PCC6803 was transformed by a spontaneous transformation method, and the resultant material was selected by kanamycin resistance. In this way, a Δslr0168::NoKASII strain, in which the construct for NoKASII gene expression was introduced into the slr0168 region on a genome of *Synechocystis* sp. strain PCC6803.

Preparation Example 2 Preparation of a Transformant Formed by Introducing, into Cyanobacteria, a NoKASII Gene from which a Chloroplast Transit Signal was Deleted A cDNA library prepared from a *Nannochloropsis oculata* strain NIES-2145 was used as a template, and PCR was carried out by using the primer Pcpc560/NoKASII(-40)-F (SEQ ID NO: 21) and the primer Trbc/NoKASII-R (SEQ ID NO: 20) described in Table 1 to amplify a NoKASII gene fragment (a NoKASII(-40) fragment, a nucleotide sequence (nucleotide sequence set forth in SEQ ID NO: 45) to which a start codon (ATG) was added on a side of a 5' end of a nucleotide sequence of the $121^{st}$ to $1428^{th}$ nucleotides of the nucleotide sequence set forth in SEQ ID NO: 2), from which a chloroplast transit signal was deleted.

A pUC118-slr0168::Pcpc560-NoKASII(-40)-Trbc-Km plasmid into which a cpc560 promoter, the NoKASII(-40) fragment, a rbc terminator and the Kanamycin-resistant gene cassette were inserted in this order into a neutral site slr0168 region derived from a *Synechocystis* sp. strain PCC6803 was obtained in the same manner as in Preparation Example 1 except that the NoKASII(-40) fragment was used in place of the NoKASII fragment.

Then, a Δslr0168::NoKASII(-40) strain was obtained by transforming the *Synechocystis* sp. strain PCC6803 in the same manner as in Preparation Example 1 except that the pUC118-slr0168::Pcpc560-NoKASII(-40)-Trbc-Km plasmid was used in place of the pUC118-slr0168::Pcpc560-NoKASII-Trbc-Km plasmid.

Preparation Example 3 Preparation of a Transformant Formed by Introducing, into Cyanobacteria, a NoKASII Gene Derived from *Arabidopsis thaliana*

A cDNA library prepared from a *Arabidopsis thaliana* was used as a template, and PCR was carried out by using the primer Pcpc560/AtKASII-F (SEQ ID NO: 22) and the primer Trbc/AtKASII-R (SEQ ID NO: 23) described in Table 1 to amplify a KAS II gene fragment (a AtKASII fragment, NCBI Gene ID 843835, SEQ ID NO: 24) encoding a KAS II gene derived from *Arabidopsis thaliana*.

A pUC118-slr0168::Pcpc560-AtKASII-Trbc-Km plasmid into which a cpc560 promoter, the AtKASII fragment, a rbc terminator and a Kanamycin-resistant gene cassette were inserted in this order into a neutral site slr0168 region derived from a *Synechocystis* sp. strain PCC6803 was obtained in the same manner as in Preparation Example 1 except that the AtKASII fragment was used in place of the NoKASII fragment.

Then, a Δslr0168::AtKASII strain was obtained by transforming the *Synechocystis* sp. strain PCC6803 in the same manner as in Preparation Example 1 except that the pUC118-slr0168::Pcpc560-AtKASII-Trbc-Km plasmid was used in place of the pUC118-slr0168::Pcpc560-NoKASII-Trbc-Km plasmid.

Test Example 1 Lipid Production

In a 20 mL Erlenmeyer flask to which 10 mL of BG-11 medium having the composition shown in Table 3 below was added, the transformants prepared in Preparation Examples 1 to 3, and *Synechocystis* sp. strain PCC6803 (wild type strain) were cultured for ten days. The cultures were conducted by using a rotary shaker (120 rpm) at 30° C. under predetermined lighting (60 μE·m$^{-2}$·sec$^{-1}$), and an initial bacterial cell concentration set to 0.4 in OD$_{730}$. In addition, kanamycin was added to the BG-11 medium for cultivation of the transformants to be 25 μg/mL in a concentration.

TABLE 3

Composition of BG-11 liquid medium

| Stock solution | |
|---|---|
| A solution | 2 mL |
| B solution | 50 mL |
| C solution | 2 mL |
| D solution | 1 mL |
| E solution | 1 mL |
| 1.0M TES—KOH (pH 7.5) | 20 mL |
| Total | 1000 mL |

TABLE 3-continued

| Composition of stock solution | |
|---|---|
| A solution | |
| Citric acid•H$_2$O | 0.33 g |
| Ferric ammonium citrate | 0.3 g |
| Na$_2$EDTA | 0.05 g |
| total | 100 mL |
| B solution | |
| NaNO$_3$ | 30 g |
| K$_2$HPO$_4$ | 0.78 g |
| MgSO$_4$•7H$_2$O | 1.5 g |
| total | 100 mL |
| C solution CaCl$_2$•2H$_2$O | 1.9 g/100 mL |
| D solution Na$_2$CO$_3$ | 2 g/100 mL |
| E solution | [H$_3$BO$_3$ 2.86 g, MnCl$_2$•4H$_2$O 1.81 g, ZnSO$_4$•7H$_2$O 0.22 g, CuSO$_4$•5H$_2$O 0.08 g, Na$_2$MoO$_4$ 0.021 g, Co(NO$_3$)•6H$_2$O 0.0494 g, H$_2$SO$_4$ single drop, H$_2$O]/1000 mL |

After completion of the cultivation, 5 mL of culture fluid was separated into a glass test tube, and concentrated by centrifuging the fluid at 3,000 rpm. A precipitate obtained by removing a supernatant was suspended into 0.5 mL of distilled water, and as an internal standard, 50 μL of 7-pentadecanone (1 mg/mL) dissolved in methanol was added thereto. Then, 0.5 mL of chloroform and 1 mL of methanol were added thereto, and the resultant mixture was stirred and further left to stand for 30 minutes. Then, 0.5 mL of chloroform and 0.5 mL of 1.5% KCl solution were added thereto, and the resultant mixture was stirred. The resultant mixture was centrifuged at 3,000 rpm for 15 minutes at room temperature, and then an organic layer (lower layer) was collected into a test tube with cap by using a Pasteur pipette, and dried and solidified by a nitrogen gas.

To a dried and solidified lipid fraction, 0.7 mL of 0.5 N KOH methanol solution was added, and the resultant mixture was stirred and kept at a constant temperature of 80° C. for 30 minutes. Further, 1 mL of boron trifluoride-methanol solution was added thereto, and a methyl esterification reaction was carried out thereon at 80° C. for 10 minutes. To this reaction fluid, 0.5 mL of hexane and 1 mL of saturated saline solution were added and the resultant mixture was stirred and left to stand for 10 minutes at room temperature, and then a hexane layer being an upper layer was collected to obtain fatty acid methyl ester.

Under the measuring conditions as follows, the obtained fatty acid methyl esters were provided for gas chromatographic analysis.

(Analysis Conditions)
Analysis apparatus: 7890A GC system (Agilent)
Capillary column: DB-WAX 20 m×100 μm×0.10 μm (J&W Scientific)
Mobile phase: high purity helium
Flow rate inside the column: 0.3 mL/min
Temperature rise program: 100° C. (for 1 min)→12.5° C./min (to 200° C.)→5° C./min (to 250° C.)→250° C. (for 9 min)
Equilibration time: for 0.5 min
Injection method: split injection (split ratio: 50:1)

Pressure: 57.308 psi
Amount of injection: 5 μL
Cleaning vial: methanol/chloroform
Detector temperature: 350° C.

The fatty acid methyl esters were identified by providing the identical sample for gas chromatography—mass spectrometry analysis under identical conditions described above.

A proportion (%) of an amount of each fatty acid in the total amount of fatty acids in each transformant was calculated from a peak area of waveform data obtained by gas chromatographic analysis. Table 4 shows the results. The results in Table 4 are shown in terms of an average value and a standard deviation in a series of three culture experiments carried out under the same conditions.

TABLE 4

Proportion of the amount of each fatty acid (% of total fatty acid)

| Genotype | C16:0 | C16:1 | C17:0 | C17:1 | C18:0 | C18:1 | C18:2 | C18:3 | C20:0 | C20:1 | C20:2 | C20:3 | C22:0 |
|---|---|---|---|---|---|---|---|---|---|---|---|---|---|
| Wild type | 53.95 ± 0.42 | 7.11 ± 0.19 | 1.20 ± 0.05 | 0.97 ± 0.04 | 0.83 ± 0.06 | 6.46 ± 0.41 | 13.54 ± 0.17 | 15.94 ± 0.17 | ND | ND | ND | ND | ND |
| Δslr0168::NoKASII | 45.68 ± 0.34 | 5.62 ± 0.04 | 0.48 ± 0.05 | 0.48 ± 0.01 | 0.99 ± 0.07 | 8.79 ± 0.40 | 19.74 ± 0.25 | 15.50 ± 0.21 | 1.40 ± 0.59 | 0.27 ± 0.02 | 0.28 ± 0.01 | 0.49 ± 0.05 | 0.28 ± 0.02 |
| Δslr0168::NoKASII(−40) | 46.17 ± 0.15 | 5.61 ± 0.13 | 0.49 ± 0.05 | 0.54 ± 0.00 | 1.38 ± 0.05 | 13.61 ± 0.81 | 15.42 ± 0.58 | 12.06 ± 0.29 | 2.62 ± 0.06 | 0.45 ± 0.06 | 0.37 ± 0.03 | 0.78 ± 0.11 | 0.52 ± 0.04 |
| Δslr0168::AtKASII | 54.13 ± 0.09 | 7.10 ± 0.07 | 1.39 ± 0.06 | 0.97 ± 0.02 | 0.73 ± 0.01 | 7.27 ± 0.07 | 14.03 ± 0.08 | 14.38 ± 0.11 | ND | ND | ND | ND | ND |

ND: not detected

As shown in Table 4, the *Synechocystis* sp. strain PCC6803 has an ability to produce fatty acids having 18 or less carbon atoms but has no ability to produce long-chain fatty acids having 20 or more carbon atoms.

In contrast, as shown in Table 4, the *Synechocystis* sp. strain PCC6803 acquires the ability to produce the long-chain fatty acids having 20 or more carbon atoms by introducing the NoKASII gene derived from *Nannochloropsis oculata* thereinto. In particular, in the transformant formed by introducing, into the cyanobacteria, the NoKASII gene from which the chloroplast transit signal was deleted, production amounts of the long-chain fatty acids having 20 or more carbon atoms were further increased.

On the other hand, even if the AtKASII gene derived from *Arabidopsis thaliana* was introduced into the *Synechocystis* sp. strain PCC6803, production of the long-chain fatty acids having 20 or more carbon atoms was unable to be detected.

Preparation Example 4 Preparation of a Transformant Which is Obtained by Introducing NoKASII Gene Into Cyanobacteria (1) Construction of Plasmid for Kanamycin Resistance Gene Expression Using genome DNA of the wild-type strains of *Synechococcus elongatus* sp. PCC7942 as a template, and the primer pUC118/NS1up-F (SEQ ID NO: 25) and the primer Krnr/NS1up-R (SEQ ID NO: 26) described in Table 2, PCR was carried out to amplify the upstream fragment of a neutral site NS1 region (NS1up fragment; SEQ ID NO: 27). Further, using the genome DNA described above, and the primer Kmr/NS1down-F (SEQ ID NO: 28) and the primer pUC118/NS1down-R (SEQ ID NO: 29) described in Table 2, PCR was carried out to amplify the downstream fragment of a neutral site NS1 region (NS1down fragment; SEQ ID NO: 30).

A pUC118-NS1::Km plasmid was obtained by inserting the NS1up fragment, NS1down fragment, and Kmr fragment prepared by a method in a manner similar to that described in Preparation Example 1 into a place between the HincII sites of the pUC118 plasmid (manufactured by Takara Bio) by using the In-Fusion (registered trademark) PCR cloning method (Clontech).

(2) Construction of a Plasmid for NoKASII Gene Expression

The pUC118-NS1::Km plasmid was used as a template, and PCR was carried out by using the primer Kmr-R (SEQ ID NO: 10) described in Table 1 and the primer NS1down-F (SEQ ID NO: 31) described in Table 2 to linearize the pUC118-NS1::Km plasmid.

Then, using a trc promoter sequence, which was artificially synthesized form the sequence of a pTrc99A cloning vector (NCBI Accession number M22744), as a template, and the primer Kmr/Ptrc-F (SEQ ID NO: 32) and the primer Ptrc-R(SEQ ID NO: 33) described in Table 2, PCR was carried out to amplify a Ptrc fragment (SEQ ID NO: 34).

Further, PCR was carried out by using genome DNA of the wild-type strains of *Synechocystis* sp. strain PCC6803, and the primer Trbc-F (SEQ ID NO: 16) and the primer NS1down/Trbc-R (SEQ ID NO: 35) described in Table 1 to amplify a Trbc fragment (SEQ ID NO: 18).

Furthermore, using a cDNA library prepared from *Nannochioropsis oculata* strain NIES-2145 as a template, and the primer Ptrc/NoKASII-F (SEQ ID NO: 36) and the primer Trbc/NoKASII-R (SEQ ID NO: 20) described in Table 2, PCR was carried out to amplify a NoKASII fragment (SEQ ID NO: 2).

Then, the linearized pUC118-NS1::Km plasmid, the Ptrc fragment, the Trbc fragment, and the NoKASII fragment were mixed, and the resultant mixture was cloned by using the In-Fusion (registered trademark) PCR Cloning method (Clontech) to obtain a pUC118-NS1::Km-Ptrc-NoKASII-Trbc plasmids in which the kanamycin resistance gene cassette, the trc promoter region, the NoKASII gene, and the rbc terminator were inserted in this order into a neutral site NS1 region derived from *Synechococcus elongatus* sp. PCC7942 strain.

(3) Transformation of Cyanobacteria Using the Plasmid for NoKASII Gene expression Using thus-obtained pUC118-NS1::Km-Ptrc-NoKASII-Trbc plasmid, *Synechococcus elongatus* sp. strain PCC7942 was transformed by a spontaneous transformation method, and the resultant material was selected by kanamycin resistance. In this way, a ΔNS1::NoKASII strain, in which the construct for NoKASII gene expression was introduced into the NS1 region on a genome of *Synechococcus elongatus* sp. strain PCC7942.

Preparation Example 5 Preparation of a Transformant Formed by Introducing, into Cyanobacteria, a NoKASII Gene from which a Chloroplast Transit Signal was Deleted A cDNA library prepared from a *Nannochloropsis oculata* strain NIES-2145 was used as a template, and PCR was carried out by using the primer Ptrc/NoKASII(-40)-F (SEQ ID NO: 37) and the primer Trbc/NoKASII-R (SEQ ID NO: 20) described in Table 2 to amplify a NoKASII gene fragment (a NoKASII(-40) fragment, a nucleotide sequence (nucleotide sequence set forth in SEQ ID NO: 45) to which a start codon (ATG) was added on a side of a 5' end of a nucleotide sequence of the $121^{st}$ to $1428^{th}$ nucleotides of the nucleotide sequence set forth in SEQ ID NO: 2), from which a chloroplast transit signal was deleted.

A pUC118-NS1::Km-Ptrc-NoKASII(-40)-Trbc plasmid into which the Kanamycin-resistant gene cassette, a trc promoter, the NoKASII(-40) fragment, and a rbc terminator were inserted in this order into a neutral site NS1 region derived from a *Synechococcus elongatus* sp. strain PCC7942 was obtained in the same manner as in Preparation Example 4 except that the NoKASII(-40) fragment was used in place of the NoKASII fragment.

Then, a ΔNS1::NoKASII(-40) strain was obtained by transforming the *Synechococcus elongatus* sp. strain PCC7942 in the same manner as in Preparation Example 4 except that the pUC118-NS1::Km-Ptrc-NoKASII(-40)-Trbc plasmid was used in place of the pUC118-NS1::Km-Ptrc-NoKASII-Trbc plasmid.

Preparation Example 6 Preparation of a Transformant Formed by Introducing, into Cyanobacteria, a KAS II Gene Derived from *Arabidopsis thaliana*

A cDNA library prepared from a *Arabidopsis thaliana* was used as a template, and PCR was carried out by using the primer Ptrc/AtKASII-F (SEQ ID NO: 38) described in Table 2 and the primer Trbc/AtKASII-R (SEQ ID NO: 23) described in Table 1 to amplify a KAS II gene fragment (a AtKASII fragment, NCBI Gene ID 843835, SEQ ID NO: 24) encoding a KAS II (SEQ ID NO: 42) derived from *Arabidopsis thaliana*.

A pUC118-NS1::Km-Ptrc-AtKASII-Trbc plasmid into which the Kanamycin-resistant gene cassette, a trc promoter, the AtKASII gene, and a rbc terminator were inserted in this order into a neutral site NS1 region derived from a *Synechococcus elongatus* sp. strain PCC7942 was obtained in the same manner as in Preparation Example 5 except that the AtKASII fragment was used in place of the NoKASII fragment.

Then, a ΔNS1::AtKASII strain was obtained by transforming the *Synechococcus elongatus* sp. strain PCC7942 in the same manner as in Preparation Example 4 except that the pUC118-NS1::Km-Ptrc-AtKASII-Trbc plasmid was used in place of the pUC118-NS1::Km-Ptrc-NoKASII-Trbc plasmid.

Preparation Example 7 Preparation of a Transformant Formed by Introducing, into Cyanobacteria, a KAS II Gene Derived from *Escherichia coli*

Genome DNA prepared from a *Escherichia coli* strain K12 was used as a template, and PCR was carried out by using the primer Ptrc/EcKASII-F (SEQ ID NO: 39) and the primer Trbc/EcKASII-R (SEQ ID NO: 40) described in Table 2 to amplify a KAS II gene fragment (a EcKASII fragment, EcoGene Accession Number EG12606, SEQ ID NO: 41) encoding a KAS II (SEQ ID NO: 43) derived from *Escherichia coli*.

A pUC118-NS1::Km-Ptrc-EcKASII-Trbc plasmid into which the Kanamycin-resistant gene cassette, a trc promoter, the EcKASII gene, and a rbc terminator were inserted in this order into a neutral site NS1 region derived from a *Synechococcus elongatus* sp. PCC7942 was obtained in the same manner as in Preparation Example 5 except that the EcKASII fragment was used in place of the NoKASII fragment.

Then, a ΔNS1::EcKASII strain was obtained by transforming the *Synechococcus elongatus* sp. strain PCC7942 in the same manner as in Preparation Example 4 except that the pUC118-NS1::Km-Ptrc-EcKASII-Trbc plasmid was used in place of the pUC118-NS1::Km-Ptrc-NoKASII-Trbc plasmid.

Test Example 2 Lipid Production

With regard to the transformants prepared in Preparation Examples 4 to 7 and the *Synechococcus elongatus* sp. strain PCC7942 (wild-type strain), lipids were produced by culturing under the same conditions as in Test Example 1.

After completion of the cultivation, a proportion (%) of an amount of each fatty acid in the total amount of fatty acids was calculated in the same manner as in Test Example 1. Table 5 shows the results

TABLE 5

| Genotype | \multicolumn{13}{c}{Proportion of the amount of each fatty acid (% of total fatty acid)} |
|---|---|---|---|---|---|---|---|---|---|---|---|---|---|
| | C14:0 | C14:1 | C16:0 | C16:1 | C17:0 | C17:1 | C18:0 | C18:1 | C20:0 | C20:1 | C22:0 | C22:1 | C24:0 |
| Wild type | 1.37 ± 0.07 | 1.32 ± 0.01 | 48.50 ± 3.49 | 37.06 ± 4.07 | 0.14 ± 0.01 | 1.29 ± 0.05 | 0.74 ± 0.06 | 9.58 ± 0.45 | ND | ND | ND | ND | ND |
| ΔNS1::NoKASII | 0.73 ± 0.01 | 0.27 ± 0.04 | 45.77 ± 0.19 | 33.19 ± 1.51 | 0.11 ± 0.00 | 0.76 ± 0.01 | 1.04 ± 0.13 | 16.74 ± 1.26 | 0.32 ± 0.07 | 0.79 ± 0.16 | 0.16 ± 0.14 | 0.10 ± 0.04 | ND |
| ΔNS1::NoKASII(-40) | 0.57 ± 0.05 | ND | 44.78 ± 0.39 | 32.20 ± 1.12 | 0.12 ± 0.01 | 0.74 ± 0.01 | 1.72 ± 0.18 | 17.05 ± 0.34 | 1.30 ± 0.22 | 0.69 ± 0.02 | 0.53 ± 0.10 | 0.17 ± 0.02 | 0.12 ± 0.01 |
| ΔNS1::AtKASII | 1.40 ± 0.03 | 1.20 ± 0.08 | 44.94 ± 0.25 | 40.09 ± 0.82 | 0.10 ± 0.01 | 0.81 ± 0.02 | 0.58 ± 0.04 | 10.87 ± 0.63 | ND | ND | ND | ND | ND |
| ΔNS1::EcFabF | 1.67 ± 0.09 | 0.99 ± 0.07 | 46.16 ± 0.08 | 37.96 ± 0.63 | 0.17 ± 0.01 | 0.76 ± 0.00 | 1.28 ± 0.13 | 11.01 ± 0.58 | ND | ND | ND | ND | ND |

ND: not detected

As shown in Table 5, the *Synechococcus elongatus* sp. strain PCC7942 has the ability to produce fatty acids having 18 or less carbon atoms but has no ability to produce long-chain fatty acids having 20 or more carbon atoms.

In contrast, as shown in Table 5, the *Synechococcus elongatus* sp. strain PCC7942 acquires the ability to produce the long-chain fatty acids having 20 carbon atoms by introducing the NoKASII gene derived from the *Nannochloropsis oculata* thereinto. In particular, in the transformant formed by introducing, into the cyanobacteria, the NoKASII gene from which the chloroplast transit signal was deleted and removed, a production amount of the long-chain fatty acids having 20 carbon atoms was further increased, and the transformant also acquired an ability to produce long-chain fatty acids having 22 or more carbon atoms.

On the other hand, even if the AtKASII gene derived from *Arabidopsis thaliana* or the EcKASII gene derived from *Escherichia coli* was introduced into the *Synechococcus elongatus* sp. strain PCC7942, production of the long-chain fatty acids having 20 or more carbon atoms was unable to be detected.

As described above, the cyanobacteria acquire the ability to produce long-chain fatty acid having 20 or more carbon atoms by enhancing the expression of a gene encoding at least any one of the proteins (A) to (D) in a cyanobacteria cell. The production amount of long-chain fatty acids or lipids containing these fatty acids as components is tend to increase in comparison with the host in which the expression of the gene is not enhanced.

Therefore, a transformant can be prepared in which the productivity of long-chain fatty acids is acquired or improved by enhancing the expression of a gene encoding at least any one of the proteins (A) to (D). Further, the productivity of long-chain fatty acids or lipids containing these long-chain fatty acids as components can be improved by culturing the transformant.

Test Example

The identity of the amino acid sequence the KAS II derived from *Arabidopsis thaliana* (AtKASII) or the KAS II derived from *Escherichia coli* (EcKASII) to the amino acid sequence of the NoKASII by using a homology analysis (search homology) program of genetic information processing software Genetyx-Win. As a result, the identity of the amino acid sequence of AtKASII (SEQ ID NO: 42) to the amino acid sequence of NoKASII (SEQ ID NO: 1) was 39%. Further, the identity of the amino acid sequence of EcKASII (SEQ ID NO: 43) to the amino acid sequence of NoKASII (SEQ ID NO: 1) was 44%.

Furthermore, the identity of the nucleotide sequence of the AtKASII gene or EcKASII gene to the nucleotide sequence of the NoKASII gene were calculated. As a results, the identity of the nucleotide sequence of the AtKASII gene (SEQ ID NO: 24) to the nucleotide sequence of the NoKASII gene (SEQ ID NO: 2) was 49%. In addition, the identity of the nucleotide sequence of the EcKASII gene (SEQ ID NO: 41) to the nucleotide sequence of the NoKASII gene (SEQ ID NO: 2) was 52%.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2016-094479 filed in Japan on May 10, 2016, which is entirely herein incorporated by reference.

What is claimed is:

1. A method of producing lipids, comprising the steps of:
culturing a transformant in which the expression of a gene encoding at least one of the following proteins (A) to (D) is increased in the transformant, wherein the transformant is a transformant of a cyanobacteria cell, and producing fatty acids or lipids containing the fatty acids as components by the transformant, wherein the fatty acids that are produced comprise fatty acids have 20 or more carbon atoms,
wherein proteins (A) to (D) are:
(A) a protein consisting of the amino acid sequence set forth in SEQ ID NO: 1;
(B) a protein consisting of an amino acid sequence having 92% or more identity with the amino acid sequence of the protein (A), and having β-ketoacyl-ACP synthase activity;
(C) a protein consisting of the amino acid sequence set forth in SEQ ID NO: 44; and
(D) a protein consisting of an amino acid sequence having 95% or more identity with the amino acid sequence of the protein (C), and having β-ketoacyl-ACP synthase activity.

2. A method of increasing lipid productivity, comprising the steps of:
increasing expression of a gene encoding at least one of the following proteins (A) to (D) in a transformant of a cyanobacteria cell,
wherein, as a result of increasing expression of the gene, the cell's productivity of long-chain fatty acids or lipids containing these fatty acids as components is increased as compared to that of the cyanobacteria cell in which expression of the gene is not increased,
wherein the fatty acids that are produced comprise fatty acids having 20 or more carbon atoms,
wherein proteins (A) to (D) are:
(A) a protein consisting of the amino acid sequence set forth in SEQ ID NO: 1;
(B) a protein consisting of an amino acid sequence having 92% or more identity with the amino acid sequence of the protein (A), and having β-ketoacyl-ACP synthase activity;
(C) a protein consisting of the amino acid sequence set forth in SEQ ID NO: 44; and
(D) a protein consisting of an amino acid sequence having 95% or more identity with the amino acid sequence of the protein (C), and having β-ketoacyl-ACP synthase activity.

3. The method according to claim 1, wherein the proteins (A) to (D) are β-ketoacyl-ACP synthases having the synthetic activity of long-chain β-ketoacyl-ACP.

4. The method according to claim 1, wherein the gene encoding at least one of the proteins (A) to (D) is a gene consisting of one of the following DNAs (a) to (d):
(a) a DNA consisting of the nucleotide sequence set forth in SEQ ID NO: 2;
(b) a DNA consisting of a nucleotide sequence having 85% or more identity with the nucleotide sequence of the DNA (a) and encoding a protein having β-ketoacyl-ACP synthase activity;
(c) a DNA consisting of the nucleotide sequence set forth in SEQ ID NO: 45; and
(d) a DNA consisting of a nucleotide sequence having 85% or more identity with the nucleotide sequence of the DNA (c) and encoding a protein having β-ketoacyl-ACP synthase activity.

5. The method according to claim 1, wherein the cyanobacteria are cyanobacteria selected from the group consisting of the genus *Synechocystis*, the genus *Synechococcus*, the genus *Thermosynechococcus*, the genus *Trichodesmium*, the genus *Acaryochloris*, the genus *Crocosphaera*, and the genus *Anabaena*.

6. The method according to claim 1, wherein the fatty acids or lipids comprise a long chain saturated fatty acid having 20, 22, or 24 carbon atoms or a mono-unsaturated fatty acid, or an ester compound thereof.

7. The method according to claim 1, wherein the protein (B) is a protein consisting of an amino acid sequence having 95% or more identity with the amino acid sequence of the protein (A), and having β-ketoacyl-ACP synthase activity.

8. The method according to claim 1, wherein the protein (D) is a protein consisting of an amino acid sequence having 98% or more identity with the amino acid sequence of the protein (C), and having β-ketoacyl-ACP synthase activity.

9. A transformant of a cyanobacteria cell, wherein the expression of a gene encoding at least one of the following proteins (A) to (D) is increased in the transformant, wherein proteins (A) to (D) are:
(A) a protein consisting of the amino acid sequence set forth in SEQ ID NO: 1;
(B) a protein consisting of an amino acid sequence having 92% or more identity with the amino acid sequence of the protein (A), and having β-ketoacyl-ACP synthase activity;
(C) a protein consisting of the amino acid sequence set forth in SEQ ID NO: 44; and
(D) a protein consisting of an amino acid sequence having 95% or more identity with the amino acid sequence of the protein (C), and having β-ketoacyl-ACP synthase activity,
wherein the transformant produces fatty acids that comprise long-chain fatty acids having 20 or more carbon atoms.

10. The transformant according to claim 9, wherein the proteins (A) to (D) are β-ketoacyl-ACP synthases having long-chain β-ketoacyl-ACP synthase activity.

11. The transformant according to claim 9, wherein the gene encoding at least one of the proteins (A) to (D) is a gene consisting of one of the following DNAs (a) to (d):
(a) a DNA consisting of the nucleotide sequence set forth in SEQ ID NO: 2;
(b) a DNA consisting of a nucleotide sequence having 85% or more identity with the nucleotide sequence of the DNA (a) and encoding a protein having β-ketoacyl-ACP synthase activity;
(c) a DNA consisting of the nucleotide sequence set forth in SEQ ID NO: 45; and
(d) a DNA consisting of a nucleotide sequence having 85% or more identity with the nucleotide sequence of the DNA (c) and encoding a protein having β-ketoacyl-ACP synthase activity.

12. The transformant according to claim 9, wherein the cyanobacteria are cyanobacteria selected from the group consisting of the genus *Synechocystis*, the genus *Synechococcus*, the genus *Thermosynechococcus*, the genus *Trichodesmium*, the genus *Acaryochloris*, the genus *Crocosphaera*, and the genus *Anabaena*.

13. The transformant according to claim 9, wherein the protein (B) is a protein consisting of an amino acid sequence having 95% or more identity with the amino acid sequence of the protein (A), and having β-ketoacyl-ACP synthase activity.

14. The transformant according to claim 9, wherein the protein (D) is a protein consisting of an amino acid sequence having 98% or more identity with the amino acid sequence of the protein (C), and having β-ketoacyl-ACP synthase activity.

15. The method according to claim 2, wherein the proteins (A) to (D) are β-ketoacyl-ACP synthases having the synthetic activity of long-chain β-ketoacyl-ACP.

16. The method according to claim 2, wherein the gene encoding at least one of the proteins (A) to (D) is a gene consisting of one of the following DNAs (a) to (d):
(a) a DNA consisting of the nucleotide sequence set forth in SEQ ID NO: 2;
(b) a DNA consisting of a nucleotide sequence having 85% or more identity with the nucleotide sequence of the DNA (a) and encoding a protein having β-ketoacyl-ACP synthase activity;
(c) a DNA consisting of the nucleotide sequence set forth in SEQ ID NO: 45; and
(d) a DNA consisting of a nucleotide sequence having 85% or more identity with the nucleotide sequence of the DNA (c) and encoding a protein having β-ketoacyl-ACP synthase activity.

17. The method according to claim 2, wherein the cyanobacteria are cyanobacteria selected from the group consisting of the genus *Synechocystis*, the genus *Synechococcus*, the genus *Thermosynechococcus*, the genus *Trichodesmium*, the genus *Acaryochloris*, the genus *Crocosphaera*, and the genus *Anabaena*.

18. The method according to claim 2, wherein the fatty acids or lipids comprise a saturated fatty acid having 20, 22, or 24 carbon atoms or a mono-unsaturated fatty acid, or an ester compound thereof.

19. The method according to claim 2, wherein the protein (B) is a protein consisting of an amino acid sequence having 95% or more identity with the amino acid sequence of the protein (A), and having β-ketoacyl-ACP synthase activity.

20. The method according to claim 2, wherein the protein (D) is a protein consisting of an amino acid sequence having 98% or more identity with the amino acid sequence of the protein (C), and having β-ketoacyl-ACP synthase activity.

* * * * *